United States Patent
Gerlach et al.

(10) Patent No.: US 7,199,130 B2
(45) Date of Patent: Apr. 3, 2007

(54) SUBSTITUTED 5,6,6A, 11B-TETRAHYDRO-7-OXA-5-AZA-BENZO[C] FLUORENE-6-CARBOXYLIC ACID COMPOUNDS AS NMDA-ANTAGONISTS

(75) Inventors: Matthias Gerlach, Brachttal (DE); Michael Przewosny, Aachen (DE); Werner Guenter Englberger, Stolberg (DE); Elke Reissmueller, Bielefeld (DE); Petra Bloms-Funke, Wuerselen (DE); Corinna Maul, Aachen (DE); Utz-Peter Jagusch, Aachen (DE)

(73) Assignee: Gruenenthal GmbH, Aachen (DE)

( * ) Notice: Subject to any disclaimer, the term of this patent is extended or adjusted under 35 U.S.C. 154(b) by 89 days.

(21) Appl. No.: 10/770,126

(22) Filed: Feb. 3, 2004

(65) Prior Publication Data

US 2004/0248889 A1 Dec. 9, 2004

Related U.S. Application Data

(63) Continuation of application No. PCT/EP02/08886, filed on Aug. 5, 2002.

(30) Foreign Application Priority Data

Aug. 3, 2001 (DE) ................................. 101 37 487

(51) Int. Cl.
*A61K 31/4741* (2006.01)
*C07D 491/06* (2006.01)

(52) U.S. Cl. ........................ 514/285; 546/62; 546/47; 514/280

(58) Field of Classification Search ................ 514/285, 514/280; 546/62, 47
See application file for complete search history.

(56) References Cited

FOREIGN PATENT DOCUMENTS

| EP | 0386839 B1 | 1/1997 |
|---|---|---|
| WO | WO-9834111 A1 | 8/1998 |
| WO | WO-9842673 A1 | 10/1998 |
| WO | WO-9964411 A1 | 12/1999 |
| WO | WO-0158875 A2 | 8/2001 |

OTHER PUBLICATIONS

E. Borrione et al. "Synthesis and Cycloaddition Reactions of Ethyl Glyoxylate Imines . . ." *J. Heterocycl. Chem.* (1988) 25:1831-1835.
R.W. Carling et al. "2-Carboxytetrahydroquinolines. Conformational and stereochemical requirements for antagonism of the glycine site on the NMDA receptor" *J. Med. Chem.* (1992) 35(11):1942-1953.
International Search Report.

*Primary Examiner*—Charanjit S. Aulakh
(74) *Attorney, Agent, or Firm*—Crowell & Moring LLP

(57) ABSTRACT

Substituted 5,6,6a,11b-tetrahydro-7-oxa-5-aza-benzo[c] fluorene-6-carboxylic acid compounds, and processes for the production thereof, pharmaceutical compositions containing these compounds and the use thereof in treatment methods and for the production of pharmaceutical preparations for specific indications, in particular for the treatment of pain.

49 Claims, No Drawings

SUBSTITUTED 5,6,6A, 11B-TETRAHYDRO-7-OXA-5-AZA-BENZO[C] FLUORENE-6-CARBOXYLIC ACID COMPOUNDS AS NMDA-ANTAGONISTS

CROSS-REFERENCE TO RELATED APPLICATIONS

This application is a continuation of International Patent Application No. PCT/EP02/08886, filed Aug. 5, 2002, designating the United States of America, and published in German as WO 03/014124 A1, the entire disclosure of which is incorporated herein by reference. Priority is claimed based on Federal Republic of Germany Patent Application No. DE 101 37 487.9, filed Aug. 3, 2001.

FIELD OF THE INVENTION

The present invention relates to substituted 5,6,6a,11b-tetrahydro-7-oxa-5-aza-benzo[c]fluorene-6-carboxylic acid compounds, and to processes for the production thereof, to pharmaceutical preparations containing these compounds and to the use thereof in treatment methods and for the production of pharmaceutical preparations for specific indications, in particular for the treatment of pain.

BACKGROUND OF THE INVENTION

The treatment of chronic and non-chronic pain is of great significance in medicine. There is a worldwide requirement for effective therapeutic methods for providing tailored and targeted treatment of chronic and non-chronic pain, this being taken to mean pain treatment which is effective and satisfactory from the patient's standpoint. This is clear from the large number of scientific papers relating to applied analgesia or to basic nociception research which have recently been published.

Conventional opioids such as morphine are highly effective in treating severe to extreme pain. However, the use thereof is limited by known side-effects, for example respiratory depression, vomiting, sedation, constipation and development of tolerance. Moreover, they are less effective in treating neuropathic or incidental pain, which is in particular experienced by tumor patients.

Opioids exert their analgesic effect by binding to membrane receptors belonging to the family of G protein-coupled receptors. The biochemical and pharmacological characterization of subtypes of these receptors has prompted hopes that subtype-specific opioids may have a effect/side-effect profile which differs from that of, for example, morphine. Further pharmacological investigations have now tentatively revealed the existence of various subtypes of these opioid receptors ($\mu_1$, $\mu_2$, $\kappa_1$, $\kappa_2$, $\kappa_3$, $\delta_1$ and $\delta_2$). There are moreover further receptors and ion channels which play a substantial role in the system governing the genesis and transmission of pain. The NMDA ion channel plays a particularly important part as a substantial proportion of synaptic communication passes via this channel. This channel controls calcium ion exchange between the neuronal cell and its surroundings.

The development of the patch-clamp technique has made it possible to elucidate the physiological significance of ion channel-selective substances. It has thus been possible clearly to demonstrate the effect of NMDA antagonists on the influence of calcium ions within the cell. It has also been established that these substances themselves have their own antinociceptive potential (e.g. ketamine). One important fact is that their mode of action differs greatly from that of, for example, opiates, as NMDA antagonists act directly on the cell's calcium balance, which vitally determines the transmission of pain. For the first time, it is thus possible to treat neuropathic types of pain successfully.

Various NMDA antagonists, which in this case were tetrahydroquinoline compounds, have already been described in the articles J. Med. Chem. (1992) 35, 1954–1968, J. Med. Chem. (1992) 35, 1942–1953 and Med. Chem. Res. (1991) 1; 64–73 and the patent applications EP 386 839, WO 97/12879 A1, WO 98/07704 A1 and WO 98/42673 A1. Many possible indications, including inter alia pain therapy, were mentioned in these publications, especially in the patent applications. However, the efficacy and usability of these substances are as yet unclear and there is accordingly still a requirement for further substances.

SUMMARY OF THE INVENTION

One object underlying the invention was to provide analgesically active substances, in particular NMDA antagonists, which are suitable for treating pain, in particular including chronic and neuropathic pain. These substances should furthermore exhibit the fewest possible side-effects such as for example nausea, vomiting, dependency, respiratory depression or constipation. The present invention accordingly provides 5,6,6a,11b-tetrahydro-7-oxa-5-aza-benzo[c]fluorene-6-carboxylic acid compounds corresponding to formula I

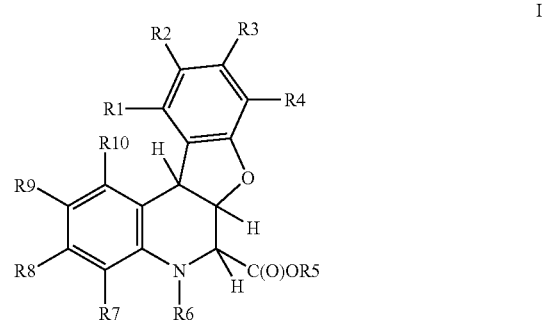

in the form as prepared or in the form of the acids or bases thereof or in the form of the salts thereof, in particular the physiologically acceptable salts, or in the form of the solvates thereof, in particular the hydrates; in particular in the form of the physiologically acceptable salts thereof with cations or bases or with anions or acids; optionally in the form of the racemates thereof, the pure stereoisomers thereof, in particular enantiomers or diastereomers, or in the form of mixtures of the stereoisomers, in particular of the enantiomers or diastereomers, in any desired mixing ratio;

in which $R^1$, $R^2$, $R^3$ and $R^4$ are mutually independently selected from among H, F, Cl, Br, I, CN, $NO_2$; $C_1$–$C_{18}$ alkyl, $C_2$–$C_{18}$ alkenyl or $C_2$–$C_{18}$ alkynyl, in each case branched or unbranched, mono- or polysubstituted or unsubstituted; $C_3$–$C_8$ cycloalkyl, saturated or unsaturated, mono- or polysubstituted or unsubstituted, or a corresponding heterocycle, in which at least one C atom in the ring is replaced by N, S or O; alkylaryl or alkylheteroaryl, in each case mono- or polysubstituted or unsubstituted; or aryl or heteroaryl, in each case mono- or polysubstituted or unsubstituted; $OR^{11}$, $OC(O)R^{11}$, $C(O)R^{11}$, $C(O)OR^{11}$, $C(O)NR^{11}R^{11\prime}$, $NR^{11}R^{11\prime}$, $S(O_2)R^{11}$ or $SR^{11}$, wherein $R^{11\prime}$ and $R^{11}$ are mutually independently selected from among H; $C_1$–$C_{18}$ alkyl, $C_2$–$C_{18}$ alkenyl or $C_2$–$C_{18}$ alkynyl, in each case branched or unbranched, mono- or polysubstituted or unsubstituted; $C_3$–$C_8$ cycloalkyl, saturated or unsaturated, mono- or polysubstituted or unsubstituted, or a corresponding heterocycle, in which at least one C atom in the ring is replaced by N, S or O; alkylaryl or alkylheteroaryl, in each case mono- or polysubstituted or unsubstituted; or aryl or heteroaryl, in each case mono- or polysubstituted or unsubstituted;

$R^5$ is selected from among

H; $C_1$–$C_{18}$ alkyl, $C_2$–$C_{18}$ alkenyl or $C_2$–$C_{18}$ alkynyl, in each case branched or unbranched, mono- or polysubstituted or unsubstituted; $C_3$–$C_8$ cycloalkyl, saturated or unsaturated, mono- or polysubstituted or unsubstituted, or a corresponding heterocycle, in which at least one C atom in the ring is replaced by N, S or O; alkylaryl or alkylheteroaryl, in each case mono- or polysubstituted or unsubstituted; or aryl or heteroaryl, in each case mono- or polysubstituted or unsubstituted;

$R^6$ is selected from among $R^{12}$ or $ZR^{12}$ with $Z = C_1$–$C_6$ alkyl, $C_2$–$C_6$ alkenyl or $C_2$–$C_6$ alkynyl, in each case branched or unbranched, mono- or polysubstituted or unsubstituted, with $R^{12}$ selected from among H; $C_1$–$C_{12}$ alkyl, $C_2$–$C_{12}$ alkenyl or $C_2$–$C_{12}$ alkynyl, in each case branched or unbranched, mono- or polysubstituted or unsubstituted; $C_3$–$C_8$ cycloalkyl, saturated or unsaturated, mono- or polysubstituted or unsubstituted, or a corresponding heterocycle, in which at least one C atom in the ring is replaced by S, O or N; or aryl or heteroaryl, in each case mono- or polysubstituted or unsubstituted;

$C(O)R^{13}$, $C(O)OR^{13}$, $C(S)R^{13}$, $C(S)OR^{13}$ or $S(O_2)R^{13}$ with $R^{13}$ selected from among H; $C_1$–$C_{10}$ alkyl, $C_2$–$C_{10}$ alkenyl or $C_2$–$C_{10}$ alkynyl, in each case branched or unbranched, mono- or polysubstituted or unsubstituted; $C_3$–$C_8$ cycloalkyl, saturated or unsaturated, mono- or polysubstituted or unsubstituted, or a corresponding heterocycle, in which at least one C atom in the ring is replaced by S, O or N; alkylaryl or alkylheteroaryl, in each case mono- or polysubstituted or unsubstituted; aryl or heteroaryl, in each case mono- or polysubstituted or unsubstituted, in particular phenethyl, 1-adamantyl, 2-adamantyl, 1-naphthyl or 2-naphthyl, 2-, 3- or 4-pyridyl; or thiazolyl;

$SR^{14}$ with $R^{14}$ selected from among aryl or heteroaryl, in each case mono- or polysubstituted or unsubstituted; or $C(O)NR^{15}R^{16}$, $C(O)NR^{15}NR^{16}R^{17}$, $C(NR^{15})NR^{16}R^{17}$, $C(S)NR^{15}R^{16}$ or $C(S)NR^{15}NR^{16}R^{17}$, wherein $R^{15}$, $R^{16}$ and $R^{17}$ are mutually independently selected from among H; $C_1$–$C_{18}$ alkyl, $C_2$–$C_{18}$ alkenyl or $C_2$–$C_{18}$ alkynyl, in each case branched or unbranched, mono- or polysubstituted or unsubstituted; $C_3$–$C_8$ cycloalkyl, saturated or unsaturated, mono- or polysubstituted or unsubstituted, or a corresponding heterocycle, in which at least one C atom in the ring is replaced by S, O or N; alkylaryl or alkylheteroaryl, in each case mono- or polysubstituted or unsubstituted; or aryl or heteroaryl, in each case mono- or polysubstituted or unsubstituted;

$R^7$, $R^8$, $R^9$ and $R^{10}$ are mutually independently selected from among H, F, Cl, Br, I, CN, $NO_2$; $C_1$–$C_{10}$ alkyl, $C_2$–$C_{10}$ alkenyl or $C_2$–$C_{10}$ alkynyl, in each case branched or unbranched, mono- or polysubstituted or unsubstituted;

$OR^{18}$, $OC(O)R^{18}$, $OC(S)R^{18}$, $C(O)R^{18}$, $C(O)OR^{18}$, $C(S)R^{18}$, $C(S)OR^{18}$, $SR^{18}$, $S(O)R^{18}$ or $S(O_2)R^{18}$, wherein $R^{18}$ is selected from among H; $C_1$–$C_{10}$ alkyl, $C_2$–$C_{10}$ alkenyl or $C_2$–$C_{10}$ alkynyl, in each case branched or unbranched, mono- or polysubstituted or unsubstituted; $C_3$–$C_8$ cycloalkyl, saturated or unsaturated, mono- or polysubstituted or unsubstituted, or a corresponding heterocycle, in which at least one C atom in the ring is replaced by S, O or N; alkylaryl or alkylheteroaryl, in each case mono- or polysubstituted or unsubstituted; or aryl or heteroaryl, in each case mono- or polysubstituted or unsubstituted;

$NR^{19}R^{20}$, $NR^{19}C(O)R^{20}$, $C(NR^{19})NR^{20}R^{21}$, $NR^{19}C(S)R^{20}$, $C(S)NR^{19}R^{20}$ or $C(S)NR^{19}NR^{20}R^{21}$ or $S(O_2)NR^{19}R^{20}$, wherein $R^{19}$, $R^{20}$ and $R^{21\prime}$ are mutually independently selected from among H, O; $C_1$–$C_{18}$ alkyl, $C_2$–$C_{18}$ alkenyl or $C_2$–$C_{18}$ alkynyl, in each case branched or unbranched, mono- or polysubstituted or unsubstituted; $C_3$–$C_8$ cycloalkyl, saturated or unsaturated, mono- or polysubstituted or unsubstituted, or a corresponding heterocycle, in which at least one C atom in the ring is replaced by S, O or N, alkylaryl or alkylheteroaryl, in each case mono- or polysubstituted or unsubstituted; or aryl or heteroaryl, in each case mono- or polysubstituted or unsubstituted; or $R^{19}$ and $R^{20}$ or $R^{20}$ and $R^{21}$ together form a $C_3$–$C_8$ cycloalkyl, saturated or unsaturated, mono- or polysubstituted or unsubstituted, or a corresponding heterocycle, in which at least one C atom in the ring is replaced by S, O or N; or $R^7$ and $R^8$, $R^8$ and $R^9$ or $R^9$ and $R^{10}$ together form $=CR^{22}$—CH=CH—CH= or =CH—$CR^{22}$=CH—CH=, with $R^{22}$ selected from among H, F, Cl, Br, I, OH or $C_1$–$C_{10}$ alkyl, $C_2$–$C_{10}$ alkenyl or $C_2$–$C_{10}$ alkynyl, in each case branched or unbranched, mono- or polysubstituted or unsubstituted.

The 5,6,6a, 11b-tetrahydro-7-oxa-5-aza-benzo [c]fluorene-6-carboxylic acid compounds according to the invention exhibit a distinct analgesic action and are also NMDA antagonists, which selectively attack the glycine-binding site.

For the purposes of the present invention alkyl or cycloalkyl residues are taken to mean saturated and unsaturated (but not aromatic), branched, unbranched and cyclic hydrocarbons, which may be unsubstituted or mono- or polysubstituted. $C_{1-2}$ alkyl here denotes C1 or C2 alkyl, $C_{1-3}$ alkyl denotes C1, C2 or C3 alkyl, $C_{1-4}$ alkyl denotes C1, C2, C3 or C4 alkyl, $C_{1-5}$ alkyl denotes C1, C2, C3, C4 or C5 alkyl, $C_{1-6}$ alkyl denotes C1, C2, C3, C4, C5 or C6 alkyl, $C_{1-7}$ alkyl denotes C1, C2, C3, C4, C5, C6 or C7 alkyl, $C_{1-8}$ alkyl denotes C1, C2, C3, C4, C5, C6, C7 or C8 alkyl, $C_{1-10}$ alkyl denotes C1, C2, C3, C4, C5, C6, C7, C8, C9 or $C_{10}$ alkyl and $C_{1-18}$ alkyl denotes C1, C2, C3, C4, C5, C6, C7, C8, C9, C10, C11, C12, C13, C14, C15, C16, C17 or C18 alkyl. $C_{3-4}$ cycloalkyl furthermore denotes C3 or C4 cycloalkyl, $C_{3-5}$ cycloalkyl denotes C3, C4 or C5 cycloalkyl, $C_{3-6}$ cycloalkyl denotes C3, C4, C5 or C6 cycloalkyl, $C_{3-7}$ cycloalkyl denotes C3, C4, C5, C6 or C7 cycloalkyl, $C_{3-8}$ cycloalkyl denotes C3, C4, C5, C6, C7 or C8 cycloalkyl, $C_{4-5}$ cycloalkyl denotes C4 or C5 cycloalkyl, $C_{4-6}$ cycloalkyl denotes C4, C5 or C6 cycloalkyl, $C_{4-7}$ cycloalkyl denotes C4, C5, C6 or C7 cycloalkyl, $C_{5-6}$ cycloalkyl denotes C5 or C6 cycloalkyl and $C_{5-7}$ cycloalkyl denotes C5, C6 or C7 cycloalkyl. With regard to cycloalkyl, the term also includes saturated cycloalkyls in which one or 2 carbon atoms are replaced by a heteroatom S, N or O. The term cycloalkyl in particular, however, also includes mono- or polyunsaturated, preferably monounsaturated, cycloalkyls without a heteroatom in the ring, provided that the cycloalkyl does not constitute an aromatic system. The alkyl or cycloalkyl residues are preferably methyl, ethyl, vinyl (ethenyl), propyl, allyl (2-propenyl), 1-propynyl, methylethyl, butyl, 1-methylpropyl, 2-methylpropyl, 1,1-dimethylethyl, pentyl, 1,1-dimethylpropyl, 1,2-dimethylpropyl, 2,2-dimethylpropyl, hexyl, 1-methylpentyl, cyclopropyl, 2-methylcyclopropyl, cyclopropylmethyl, cyclobutyl, cyclopentyl, cyclopentylmethyl, cyclohexyl, cycloheptyl, cyclooctyl, as well as adamantyl, $CHF_2$, $CF_3$ or $CH_2OH$ and pyrazolinone, oxopyrazolinone, [1,4]-dioxane or dioxolane.

In relation to alkyl and cycloalkyl, it is here understood that, unless explicitly stated otherwise, for the purposes of the present invention, substituted means the substitution of a hydrogen residue by F, Cl, Br, I, $NH_2$, SH or OH, wherein "polysubstituted" residues should be taken to mean that substitution is performed repeatedly both on different and the same atoms with identical or different substituents, for example three times on the same C atom as in case of $CF_3$ or on different sites as in the case of —CH(OH)—CH=CH—$CHCl_2$. Particularly preferred substituents are here F, Cl and OH.

The term $(CH_2)_{3-6}$ should be taken to mean —$CH_2$—$CH_2$—$CH_2$—, —$CH_2$—$CH_2$—$CH_2$—$CH_2$—, —$CH_2$—$CH_2$—$CH_2$—$CH_2$—$CH_2$— and —$CH_2$—$CH_2$—$CH_2$—$CH_2$—$CH_2$—$CH_2$—, while the term $(CH_2)_{1-4}$ should be taken to mean —$CH_2$—, —$CH_2$—$CH_2$—, —$CH_2$—$CH_2$—$CH_2$— and —$CH_2$—$CH_2$—$CH_2$—$CH_2$—, etc.

An aryl residue is taken to mean ring systems comprising at least one aromatic ring, but without a heteroatom in even one of the rings. Examples are phenyl, naphthyl, fluoranthenyl, fluorenyl, tetralinyl or indanyl, in particular 9H fluorenyl or anthacenyl residues, which may be unsubstituted or mono- or polysubstituted.

A heteroaryl residue is taken to mean heterocyclic ring systems comprising at least one unsaturated ring, which contain one or more heteroatoms from the group comprising nitrogen, oxygen and/or sulfur and may also be mono- or polysubstituted. Examples from the group of heteroaryls which may be mentioned are furan, benzofuran, thiophene, benzothiophene, pyrrole, pyridine, pyrimidine, pyrazine, quinoline, isoquinoline, phthalazine, benzo-1,2,5-thiadiazole, benzothiazole, indole, benzotriazole, benzodioxolane, benzodioxane, carbazole, indole and quinazoline.

In relation to aryl and heteroaryl, substituted is taken to mean the substitution of the aryl or heteroaryl with $R^{23}$, $OR^{23}$, a halogen, preferably F and/or Cl, a $CF_3$, a CN, an $NO_2$, an $NR^{24}R^{25}$, a $C_{1-6}$ alkyl (saturated), a $C_{1-6}$ alkoxy, a $C_{3-8}$ cycloalkoxy, a $C_{3-8}$ cycloalkyl or a $C_{2-6}$ alkylene.

The residue $R^{23}$ here denotes H, a $C_{1-10}$ alkyl, preferably a $C_{1-6}$ alkyl, an aryl or heteroaryl or an aryl or heteroaryl residue attached via a $C_{1-3}$ alkylene group, wherein these aryl and heteroaryl residues may not themselves be substituted with aryl or heteroaryl residues.

The residues $R^{24}$ and $R^{25}$ may be identical or different and denote H, a $C_{1-10}$ alkyl, preferably a $C_{1-6}$ alkyl, an aryl, a heteroaryl or an aryl or heteroaryl attached via a $C_{1-3}$ alkylene group, wherein these aryl and heteroaryl residues may not themselves be substituted with aryl or heteroaryl residues, or the residues $R^{24}$ and $R^{25}$ together mean $CH_2CH_2OCH_2CH_2$, $CH_2CH_2NR^{26}CH_2CH_2$ or $(CH_2)_{3-6}$.

The residue $R^{26}$ denotes H, a $C_{1-10}$ alkyl, preferably a $C_{1-6}$ alkyl, an aryl or heteroaryl residue or an aryl or heteroaryl residue attached via a $C_{1-3}$ alkylene group, where these aryl and heteroaryl residues may not themselves be substituted with aryl or heteroaryl residues.

The term salt should be taken to mean any form of the active substance according to the invention, in which the latter assumes ionic form or bears a charge and is coupled with a counterion (a cation or anion) or is in solution. These should also be taken to mean complexes of the active substance with other molecules and ions, in particular complexes which are complexed by means of ionic interactions.

For the purposes of the present invention, a physiologically acceptable salt with cations or bases is taken to mean salts of at least one of the compounds according to the invention, usually a (deprotonated) acid, as the anion with at least one, preferably inorganic, cation, which is physiologically acceptable, in particular for use in humans and/or mammals. Particularly preferred salts are those of the alkali and alkaline earth metals, as are those with $NH_4+$, most particularly preferred are (mono-) or (di-)sodium, (mono-) or (di-)potassium, magnesium or calcium salts.

For the purposes of the present invention, a physiologically acceptable salt with anions or acids is taken to mean salts of at least one of the compounds according to the invention, usually protonated, for example on the nitrogen, as the cation with at least one anion, which is physiologically acceptable, in particular for use in humans and/or mammals. In particular, for the purposes of the present invention, the physiologically acceptable salt is taken to be the salt formed with a physiologically acceptable acid, namely salts of the particular active substance with inorganic or organic acids which are physiologically acceptable, in particular for use in humans and/or mammals. Examples of physiologically acceptable salts of certain acids are salts of: hydrochloric acid, hydrobromic acid, sulfuric acid, methanesulfonic acid, formic acid, acetic acid, oxalic acid, succinic acid, tartaric acid, mandelic acid, fumaric acid, lactic acid, citric acid, glutamic acid, 1,1-dioxo-1,2-dihydro-1,6-benzo[d]isothiazol-3-one (saccharinic acid), monomethylsebacic acid, 5-oxo-proline, hexane-1-sulfonic acid, nicotinic acid, 2-, 3- or 4-aminobenzoic acid, 2,4,6-trimethylbenzoic acid, α-lipoic acid, acetylglycine, acetylsalicylic acid, hippuric acid and/or aspartic acid. The hydrochloride salt is particularly preferred.

The present application preferably provides substituted 5,6,6a,11b-tetrahydro-7-oxa-5-aza-benzo[c]fluorene-6-carboxylic acid compounds of the formula I, in which $R^6$ is selected from among H; $C_1$–$C_{10}$ alkyl, unsubstituted or mono- or polysubstituted; phenyl, unsubstituted or mono- or polysubstituted; preferably H, $CH_3$ or $C_2H_5$, in particular H.

The present application preferably also provides substituted 5,6,6a,11b-tetrahydro-7-oxa-5-aza-benzo[c]fluorene-6-carboxylic acid compounds of the formula I, in which $R^5$ is selected from among H; $C_1$–$C_4$ alkyl, branched or unbranched, mono- or polysubstituted or unsubstituted; phenyl, benzyl, or phenethyl, mono- or polysubstituted or unsubstituted, preferably H, $CH_3$ or $C_2H_5$, in particular H.

The present application preferably also provides substituted 5,6,6a,11b-tetrahydro-7-oxa-5-aza-benzo [c]fluorene-6-carboxylic acid compounds of the formula I, in which $R^7$, $R^8$, $R^9$ and $R^{10}$ are mutually independently selected from among H, F, Cl, Br, I, CN, NO$_2$; C$_1$–C$_6$ alkyl, C$_2$–C$_6$ alkenyl or C$_2$–C$_6$ alkynyl, in each case branched or unbranched, mono- or polysubstituted or unsubstituted;

OR$^{18}$, C(O)R$^{18}$, C(O)OR$^{18}$ or SR$^{18}$, wherein R$^{18}$ is selected from among H; C$_1$–C$_4$ alkyl, branched or unbranched, mono- or polysubstituted or unsubstituted; aryl, mono- or polysubstituted or unsubstituted, R$^7$, R$^8$, R$^9$ and R$^{10}$ are preferably mutually independently selected from among H, F, Cl, Br, I, CN; C$_1$–C$_4$ alkyl, branched or unbranched, mono- or polysubstituted or unsubstituted;

OR$^{18}$ or SR$^{18}$, with R$^{18}$ selected from among

H; C$_1$–C$_4$ alkyl, branched or unbranched, mono- or polysubstituted or unsubstituted; phenyl, mono- or polysubstituted or unsubstituted, in particular R$^7$, R$^8$, R$^9$ and R$^{10}$ are mutually independently selected from among H, F, Cl, Br, I, CN; CH$_3$, CF$_3$, t-butyl, i-butyl, OH, —OCH$_3$, —OCF$_3$, —SCH$_3$, —O-phenyl.

It is particularly preferred in this connection if
R$^7$, R$^8$ and R$^{10}$ mean H and R$^9$ means Cl or R$^7$ and R$^9$ mean H and R$^8$ and R$^{10}$ mean Cl,
preferably, R$^7$ and R$^9$ mean H and R$^8$ and R$^{10}$ mean Cl.

The present application particularly preferably provides substituted 5,6,6a,11b-tetrahydro-7-oxa-5-aza-benzo[c]fluorene-6-carboxylic acid compounds of the formula I, in which

R$^5$=H,

R$^6$=H,

R$^7$=H,

R$^8$=Cl,

R$^9$=H and

R$^{10}$=Cl.

The present application preferably also provides substituted 5,6,6a,11b-tetrahydro-7-oxa-5-aza-benzo[c]fluorene-6-carboxylic acid compounds of the formula I, in which R$^1$, R$^2$, R$^3$ or R$^4$ are mutually independently selected from among H, F, Cl, Br, I, CN, NO$_2$; C$_1$–C$_6$ alkyl, C$_2$–C$_6$ alkenyl or C$_2$–C$_6$ alkynyl, in each case branched or unbranched, mono- or polysubstituted or unsubstituted;

OR$^{11}$, OC(O)R$^{11}$, C(O)R$^{11}$, C(O)OR$^{11}$, C(O)NR$^{11}$R$^{11\prime}$, NR$^{11}$R$^{11\prime}$, S(O$_2$)R$^{11}$ or SR$^{11}$, wherein R$^{11}$ and R$^{11\prime}$ are mutually independently selected from among H; C$_1$–C$_6$ alkyl, C$_2$–C$_6$ alkenyl or C$_2$–C$_6$ alkynyl, in each case branched or unbranched, mono- or polysubstituted or unsubstituted;

preferably

H, F, Cl, Br, I, CN, NH$_2$, NO$_2$; C$_1$–C$_4$ alkyl, C$_2$–C$_4$ alkenyl or C$_2$–C$_4$ alkynyl, in each case branched or unbranched, mono- or polysubstituted or unsubstituted;

OR$^{11}$, C(O)OR$^{11}$ or SR$^{11}$, wherein R$^{11}$ is selected from among

H; C$_1$–C$_4$ alkyl, C$_2$–C$_4$ alkenyl or C$_2$–C$_4$ alkynyl, in each case branched or unbranched, mono- or polysubstituted or unsubstituted;

in particular

H, F, Cl, Br, I, CN, NH$_2$; C$_1$–C$_4$ alkyl, branched or unbranched, mono- or polysubstituted or unsubstituted; SH; OR$^{11}$ or C(O)OR$^{11}$, wherein R$^{11}$ is selected from among H; C$_1$–C$_4$ alkyl, branched or unbranched, mono- or polysubstituted or unsubstituted;

or particularly preferably

H, F, Cl, Br, I, CN, NH$_2$, CH$_3$, C$_2$H$_5$, n-propyl, i-propyl, i-butyl, sec.-butyl, n-butyl, t-butyl, CF$_3$, CHF$_2$, SH, OH, OCH$_3$, OC$_2$H$_5$, C(O)OH, C(O)OCH$_3$ or C(O)OC$_2$H$_5$.

The present invention in particular provides the following substituted 5,6,6a,11b-tetrahydro-7-oxa-5-aza-benzo[c]fluorene-6-carboxylic acid compounds or the salts thereof:

1,3-Dichloro-5,6,6a,11b-tetrahydro-7-oxa-5-aza-benzo[c]fluorene-6-carboxylic acid, 1,3-Dichloro-10-methoxy-5,6,6a,11b-tetrahydro-7-oxa-5-aza-benzo [c]fluorene-6-carboxylic acid, 1,3-Dichloro-8-methyl-5,6,6a,11b-tetrahydro-7-oxa-5-aza-benzo[c]fluorene-6-carboxylic acid, 1,3-Dichloro-8-ethyl-5,6,6a,11b-tetrahydro-7-oxa-5-aza-benzo[c]fluorene-6-carboxylic acid, 1,3-Dichloro-8-ethyl-5,6,6a,11b-tetrahydro-7-oxa-5-aza-benzo[c]fluorene-6-carboxylic acid, 1,3-Dichloro-8-fluoro-5,6,6a,11b-tetrahydro-7-oxa-5-aza-benzo [c]fluorene-6-carboxylic acid, 1,3,8-Trichloro-5,6,6a,11b-tetrahydro-7-oxa-5-aza-benzo[c]fluorene-6-carboxylic acid, 8-Bromo-1,3-dichloro-5,6,6a,11b-tetrahydro-7-oxa-5-aza-benzo[c]fluorene-6-carboxylic acid, 8-Iodo-1,3-dichloro-5,6,6a,11b-tetrahydro-7-oxa-5-aza-benzo [c]fluorene-6-carboxylic acid, 1,3-Dichloro-5,6,6a,11b-tetrahydro-7-oxa-5-aza-benzo [c]fluorene-6,8-dicarboxylic acid, 1,3-Dichloro-10-methyl-5,6,6a,11b-tetrahydro-7-oxa-5-aza-benzo [c]fluorene-6-carboxylic acid, 1,3-Dichloro-10-fluoro-5,6,6a,11b-tetrahydro-7-oxa-5-aza-benzo [c]fluorene-6-carboxylic acid, 1,3,10-Trichloro-5,6,6a,11b-tetrahydro-7-oxa-5-aza-benzo [c]fluorene-6-carboxylic acid, 10-Bromo-1,3-dichloro-5,6,6a,11b-tetrahydro-7-oxa-5-aza-benzo[c]fluorene-6-carboxylic acid, 10-Iodo-1,3-dichloro-5,6,6a,11b-tetrahydro-7-oxa-5-aza-benzo [c]fluorene-6-carboxylic acid, 1,3-Dichloro-5,6,6a,11b-tetrahydro-7-oxa-5-aza-benzo[c] fluorene-6,10-dicarboxylic acid or 1,3-Dichloro-10-cyano-5,6,6a,11b-tetrahydro-7-oxa-5-aza-benzo [c]fluorene-6-carboxylic acid, preferably 1,3-dichloro-5,6,6a,11b-tetrahydro-7-oxa-5-aza-benzo[c]fluorene-6-carboxylic acid.

Particularly preferred compounds are the free carboxylic acids or the salts of the substituted 5,6,6a,11b-tetrahydro-7-oxa-5-aza-benzo [c]fluorene-6-carboxylic acid compounds according to the invention of the formula I in the form of the alkali metal salts thereof, preferably the potassium or sodium salts, or in the form of inorganic acid salts, preferably the hydrochloride.

The present invention also provides processes for the production of the salts according to the invention of a substituted 5,6,6a,11b-tetrahydro-7-oxa-5-aza-benzo [c]fluorene-6-carboxylic acid compound.

Various processes for the preparation of tetrahydroquinolines, the parent substance of the compounds according to the invention, are described in the literature:

a solid phase approach (WO 98/34111), multistage processes (WO 98/42673; Bioorganic and Medicinal Chemistry Letters vol. 2, p. 371, 1992; Journal of Heterocyclic Chemistry vol. 25, p. 1831, 1988; Journal of the Chemical Society, Perkin Transactions 1 (1989), page 2245) or a Lewis acid-catalyzed "single vessel" process (Journal of the Chemical Society, Chemical Communications, 1999, p. 651; Journal of the American Chemical Society, vol. 118, p. 8977, 1996).

However, all these processes clearly exhibit some disadvantages.

Unlike these processes, the "basic process" described herein is a trifluoroacetic acid-mediated, preferably "single vessel" process, in which one aromatic amine component, one aldehyde component and one electron-rich olefin component react together.

The basic process involves initially producing 5,6,6a,11b-tetrahydro-7-oxa-5-aza-benzo[c]fluorene-6-carboxylic acid compounds of the formula I with $R^6$=H, while the other residues have one of the above-stated meanings. In this process, anilines corresponding to formula II, in which $R^7$, $R^8$, $R^9$ and $R^{10}$ mutually independently each and have one of the meanings already stated for formula I or are provided with a protective group,

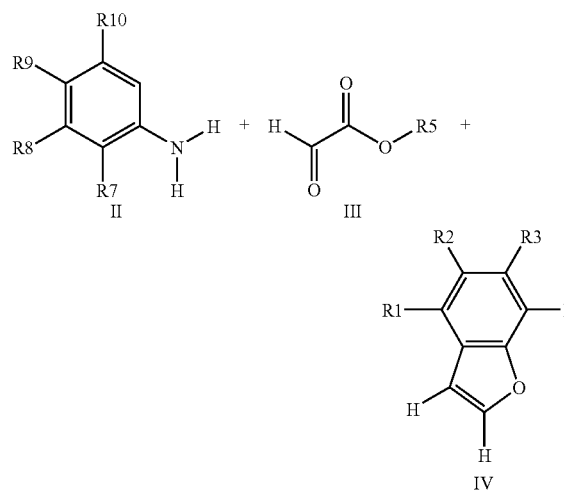

are reacted with glyoxalic acid esters or glyoxalic acid of the formula III and a benzofuran according to IV, in which $R^1$, $R^2$, $R^3$, $R^4$ and $R^5$ mutually independently each have one of the meanings already stated for formula I or are provided with a protective group, in the presence of trifluoroacetic acid at between 0° C. and 100° C. It is preferred in this connection that the duration of the reaction is 0.25–12 h, preferably at most 2 h. It is also preferred that the reaction proceeds at a temperature of between 20 and 40° C., preferably room temperature, and/or preferably the reaction is a single-vessel reaction.

A decisive advantage of the process according to the invention is that the process is highly selective and gives good yields by means of a domino reaction (imine formation followed by an aza Diels-Alder reaction).

By dispensing with the necessity of carrying out a linkage or elimination step, as in the case of the solid phase approach, and also with the necessity of purifying the intermediates, as in the case of the described solution chemistry, the process according to the invention differs with regard both to its simplicity to perform and its purification method. The products may for the most part be obtained in high purity by repeated washing with nonpolar solvents, such as for example n-hexane. Otherwise, they are purified by means of column chromatography. In particular, compounds of the formula I may be obtained in diastereomerically pure form by washing processes with nonpolar solvents, such as for example n-hexane, or by crystallization of the salts thereof.

In general, in a favorable form of the production process, once formation of a compound of the formula I is complete, the compound is converted into a compound with a base or acid, which may already contain the desired cation or anion, and the resultant salt is then purified.

Most of the reagents used in the process, in particular of the formulae II, III and IV, are commercially available or may be produced by simple synthesis steps known to the person skilled in the art. After the basic process, the products obtained according to the basic process may be converted in accordance with methods known to the person skilled in the art into derived products according to the invention of the formula I, wherein the hydrogen on $R^6$ is initially substituted.

Accordingly, if the intended products are substituted 5,6,6a,11b-tetrahydro-7-oxa-5-aza-benzo[c]fluorene-6-carboxylic acid compounds of the formula I with $R^6$=alkylformyl, acyl, sulfenyl and sulfonyl, once the basic reaction has been performed, the reaction product may be reacted with appropriate chloro- or fluoroformates, acid chlorides, sulfenyl chlorides and sulfonyl chlorides in the presence of a base, preferably triethylamine, pyridine or NaOH, at a temperature of between 0–20° C. in water, dioxane/water or THF/water mixtures (J. Org. Chem. 1989, 54, 5574–5580). Similarly, if the intended products are substituted 5,6,6a,11b-tetrahydro-7-oxa-5-aza-benzo[c]fluorene-6-carboxylic acid compounds of the formula I with $R^6$=C(S)NR$^{15}$R$^{16}$, once the basic reaction has been performed, the reaction product may be reacted with a thionation reagent, preferably Lawesson's reagent (2,4-bis(4-methoxyphenyl)-2,4-dithioxo-1,3,2,4-dithiaphosphetane), in organic solvents, preferably THF or toluene, at a temperature of 30–50° C.

Alternatively, if the intended products are substituted 5,6,6a,11b-tetrahydro-7-oxa-5-aza-benzo[c]fluorene-6-carboxylic acid compounds of the formula I with $R^6$=C(O)NR$^{15}$R$^{16}$ or C(S)NR$^{15}$R$^{16}$, once the basic reaction has been performed, the reaction product may be reacted with potassium cyanate or potassium isothiocyanate in water at temperatures of up to 100° C. or with organic isocyanates or isothiocyanates in alcohols, preferably methanol, ethanol or isopropanol at temperatures of up to boiling point. Furthermore, if the intended products are substituted 5,6,6a,11b-tetrahydro-7-oxa-5-aza-benzo[c]fluorene-6-carboxylic acid compounds of the formula I with $R^6$=C(NR$^{15}$)NR$^{16}$R$^{17}$, once the basic reaction has been performed, the reaction product may be reacted with O-methylisoureas or S-methylisothioureas under alkaline conditions, preferably in ethanolic or methanolic NaOH or KOH, at temperatures of 20–50° C.

Furthermore, if the intended products are substituted 5,6,6a,11b-tetrahydro-7-oxa-5-aza-benzo[c]fluorene-6-carboxylic acid compounds of the formula I with $R^6$=C(O)NR$^{15}$R$^{16}$, once the basic reaction has been performed, the reaction product may also be reacted with 2-propanone semicarbazone in water/glacial acetic acid at 30–60° C.

Similarly, if the intended products are substituted 5,6,6a,11b-tetrahydro-7-oxa-5-aza-benzo[c]fluorene-6-carboxylic acid compounds of the formula I with $R^6$=C(S)NR$^{15}$R$^{16}$, once the basic reaction has been performed, the reaction product may be reacted with $CS_2$ and hydrazines in water/NaOH at 30–60° C.

As the final possibility which will be mentioned in this connection, if the intended products are substituted 5,6,6a,11b-tetrahydro-7-oxa-5-aza-benzo[c]fluorene-6-carboxylic acid compounds of the formula I with $R^6$=alkyl, benzyl or phenethyl, once the basic reaction has been performed, the reaction product may be reacted with a corresponding alkylation halide, benzyl halide or phenethyl halide and a suitable base, preferably sodium hydride or potassium tert.-butylate, in a solvent, for example ethanol, between 0 and 100° C. (J. Org. Chem. 1947, 12, 760; Zh. Obshch. Khim. 1942, 12, 418).

Under many of the stated reaction conditions, OH, SH and $NH_2$ groups may possibly enter into unwanted secondary reactions. It is thus preferred to provide said groups with protective groups or, in the case of $NH_2$, to replace them with $NO_2$ and, before the final product is purified, to eliminate the protective group or reduce the $NO_2$ group. The present application accordingly also provides a modification of the above-described process, in which, in the starting compounds, at least one OH group has been replaced by an $OSi(Ph)_2$tert.-butyl group, at least one SH-group has been replaced by an S-p-methoxybenzyl group and/or at least one $NH_2$ group has been replaced by an $NO_2$ group and, before the final product is purified, at least one, preferably all, of the $OSi(Ph)_2$tert.-butyl group(s) is/are eliminated with tetrabutylammonium fluoride in tetrahydrofuran and/or at least one, preferably all, of the p-methoxybenzyl group(s) is/are eliminated with a metal amide, preferably sodium amide, and/or at least one, preferably all, of the $NO_2$ group(s) is/are reduced to $NH_2$.

Furthermore, under certain circumstances, carboxylic acid or thiocarboxylic acid groups are not stable under the reaction conditions, such that it is preferred to use the methyl ester thereof in the reactions and subsequently to saponify the product of the process with KOH solution or NaOH solution in methanol at 40° C.–60° C. The present invention accordingly also provides a modification of the above-described process in which, before the final product is purified, a product of the process with at least one $C(O)OCH_3$, $OC(O)OCH_3$ and/or $C(S)OCH_3$ group is saponified with KOH solution or NaOH solution in methanol or ethanol at 0° C.–100° C., preferably 40° C.–60° C.

It may accordingly also be favorable when producing substituted 5,6,6a,11b-tetrahydro-7-oxa-5-aza-benzo[c]fluorene-6-carboxylic acid compounds of the formula I with $R^5$=H to use starting products of the formula III for the basic process, in which $R^5 \neq H$ and $R^5$ is preferably alkyl, in particular $CH_3$ and $C_2H_5$. According to the basic process and also the subsequent reactions which possibly follow, the reaction product is saponified with an appropriate base, preferably NaOH or KOH, in ethanol or methanol, at temperatures of between 0–100° C., preferably 40° C.–60° C. (Organikum, 1990, p. 418).

In order to produce the salts, in particular the physiologically acceptable salts, with cations or bases, the following method is used: one equivalent of a compound of the formula I, preferably an imino acid, or a carboxylic acid, in particular with $R^3$=H, is suspended in a little water and one equivalent of 1 normal aqueous alkali solution, for example NaOH or KOH, is added. If solubility is poor, methanol is added dropwise until complete dissolution is achieved. After stirring at room temperature, the mixture is evaporated in a rotary evaporator, the remaining solution is frozen at low temperatures in a mixture of isopropanol/dry ice and freeze-dried. The salts, in particular the imino acids or carboxylic acids, preferably the sodium or potassium salts, are obtained as mainly colorless solids. Alternatively, it is also possible to produce the potassium or sodium salts with potassium or sodium trimethylsilanolate (E. D. Laganis, B. L. Chenard; Tetrahedron Letters 25, 5831–5834 (1984)). In this case, potassium or sodium trimethylsilanolate is dissolved under nitrogen in an organic solvent (for example, dichloromethane, toluene or THF) and the ester or the acid is added in a single portion. The reaction mixture is stirred for two or more hours at room temperature and filtered out. The mainly colorless solid is washed and dried under a vacuum. The potassium or sodium salts are obtained as solids.

The substituted 5,6,6a,11b-tetrahydro-7-oxa-5-aza-benzo[c]fluorene-6-carboxylic acid compounds according to the invention are toxicologically safe, such that they are suitable as a pharmaceutically active ingredient in pharmaceutical preparations.

The present invention accordingly also provides a pharmaceutical preparation containing as active ingredient at least one substituted 5,6,6a,11b-tetrahydro-7-oxa-5-aza-benzo[c]fluorene-6-carboxylic acid compound according to the invention of the formula I in the form as prepared or in the form of the acid or base or in the form of the salts thereof, in particular the physiologically acceptable salts, or in the form of the solvates thereof, in particular the hydrates; in particular in the form of the physiologically acceptable salts thereof with cations or bases or with anions or acids; optionally in the form of the racemates thereof, of the pure stereoisomers thereof, in particular enantiomers or diastereomers, or in the form of mixtures of the stereoisomers, in particular the enantiomers or diastereomers, in any desired mixing ratio; and optionally containing suitable additives and/or auxiliary substances and/or optionally further active ingredients.

The pharmaceutical preparations according to the invention may be administered in the form of solutions for injection, drops or succi, as semi-solid dosage forms in the form of granules, tablets, pellets, patches, capsules, dressings or aerosols and, in addition to the at least one substituted 5,6,6a,11b-tetrahydro-7-oxa-5-aza-benzo[c]fluorene-6-carboxylic acid compound according to the invention, they also optionally contain, depending upon the pharmaceutical presentation, excipients, fillers, solvents, diluents, colorants and/or binders. Selection of the auxiliary substances and the quantities thereof which are to be used depends upon whether the pharmaceutical preparation is to be administered orally, perorally, parenterally, intravenously, intraperitoneally, intradermally, intramuscularly, intranasally, buccally, rectally or topically, for example onto infections of the skin, mucous membranes or eyes. Preparations in the form of tablets, coated tablets, capsules, granules, drops, succi and syrups are suitable for oral administration, while solutions, suspensions, easily reconstitutible dried preparations and sprays are suitable for parenteral, topical and inhalatory administration. Substituted 5,6,6a-11b-tetrahydro-7-oxa-5-aza-benzo[c]fluorene-6-carboxylic acid compounds according to the invention in a depot in dissolved form or in a dressing, optionally with the addition of skin penetration promoters, are examples of suitable percutaneous formulations. Orally or percutaneously administrable preparations may release the substituted 5,6,6a,11b-tetrahydro-7-oxa-5-aza-benzo[c]fluorene-6-carboxylic acid compounds according to the invention in a delayed manner. The quantity of active substance to be administered to the patient varies as a function of patient weight, mode of administration, the indication and the severity of the condition. Conventionally, 2 to 500 mg/kg of at least one substituted 5,6,6a,11b-tetrahydro-7-oxa-5-azabenzo[c]fluorene-6-carboxylic acid compound according to the invention of the formula I are administered.

The substituted 5,6,6a,11b-tetrahydro-7-oxa-5-aza-benzo[c]fluorene-6-carboxylic acid compounds according to the invention are preferably used for treating pain, in particular chronic and neuropathic pain, but also for migraine, such that the present invention also provides the use of at least one substituted 5,6,6a,11b-tetrahydro-7-oxa-5-aza-benzo[c]fluorene-6-carboxylic acid compound according to the invention of the formula I in the form as prepared or in the form of the acid or base or in the form of the salts thereof, in particular the physiologically acceptable salts, or in the form of the solvates thereof, in particular the hydrates; in particular in the form of the physiologically acceptable salts thereof with cations or bases or with anions or acids; optionally in the form of the racemates thereof, the pure stereoisomers thereof, in particular enantiomers or diastereomers, or in the form of mixtures of the stereoisomers, in particular the enantiomers or diastereomers, in any desired mixing ratio; for the production of a pharmaceutical preparation for the treatment of pain, in particular of neuropathic and/or chronic pain, and/or for the treatment of migraine.

Further applications arise from the affinity with the NMDA receptor, as NMDA antagonists are known, inter alia, to have a neuroprotective action and are thus well suited to use with clinical pictures associated with neurodegeneration and nerve damage, such as Parkinson's disease and Huntington's chorea etc. Further indications of the NMDA antagonists according to the invention are epilepsy, glaucoma, osteoporosis, ototoxicity, the withdrawal symptoms associated with alcohol and/or drug abuse, stroke and the associated cerebral ischemia, cerebral infarcts, cerebral edema, hypoxia, anoxia, together with use for anxiolysis and in anesthesia. The present invention accordingly also provides the use of at least one substituted 5,6,6a,11b-tetrahydro-7-oxa-5-aza-benzo[c]fluorene-6-carboxylic acid compound according to the invention of the formula I; in the form as prepared or in the form of the acid or base or in the form of the salts thereof, in particular the physiologically acceptable salts, or in the form of the solvates thereof, in particular the hydrates; in particular in the form of the physiologically acceptable salts thereof with cations or bases or with anions or acids; optionally in the form of the racemates thereof, the pure stereoisomers thereof, in particular enantiomers or diastereomers, or in the form of mixtures of the stereoisomers, in particular the enantiomers or diastereomers, in any desired mixing ratio; for the production of a pharmaceutical preparation for the treatment/prevention of epilepsy, Parkinson's disease, Huntington's chorea, glaucoma, ototoxicity, withdrawal symptoms associated with alcohol and/or drug abuse, stroke, cerebral ischemia, cerebral infarcts, cerebral edema, hypoxia, anoxia and/or for anxiolysis and/or anesthesia.

It has surprisingly been found that the substituted 5,6,6a,11b-tetrahydro-7-oxa-5-aza-benzo[c]fluorene-6-carboxylic acid compound according to the invention is also highly suitable for further indications, in particular for the treatment of urinary incontinence, pruritus, tinnitus and/or diarrhea. The present application accordingly also provides the use of at least one substituted 5,6,6a,11b-tetrahydro-7-oxa-5-aza-benzo [c]fluorene-6-carboxylic acid compound according to the invention of the formula I; in the form as prepared or in the form of the acid or base or in the form of the salts thereof, in particular the physiologically acceptable salts, or in the form of the solvates thereof, in particular the hydrates; in particular in the form of the physiologically acceptable salts thereof with cations or bases or with anions or acids; optionally in the form of the racemates thereof, the pure stereoisomers thereof, in particular enantiomers or diastereomers, or in the form of mixtures of the stereoisomers, in particular the enantiomers or diastereomers, in any desired mixing ratio; for the production of a pharmaceutical preparation for the treatment of urinary incontinence, pruritus, tinnitus and/or diarrhea.

The compounds according to the invention are, however, also effective for other indications. The present application accordingly also provides the use of at least one substituted 5,6,6a,11b-tetrahydro-7-oxa-5-aza-benzo[c]fluorene-6-carboxylic acid compound according to the invention of the formula I; in the form as prepared or in the form of the acid or base or in the form of the salts thereof, in particular the physiologically acceptable salts, or in the form of the solvates thereof, in particular the hydrates; in particular in the form of the physiologically acceptable salts thereof with cations or bases or with anions or acids; optionally in the form of the racemates thereof, the pure stereoisomers thereof, in particular enantiomers or diastereomers, or in the form of mixtures of the stereoisomers, in particular the enantiomers or diastereomers, in any desired mixing ratio; for the production of a pharmaceutical preparation for the treatment/prevention of schizophrenia, Alzheimer's disease, psychoses due to elevated amino acid levels, AIDS dementia, encephalomyelitis, Tourette's syndrome, perinatal asphyxia, inflammatory and allergic reactions, depression, drug and/or alcohol abuse, gastritis, diabetes, cardiovascular disease, respiratory diseases, coughing and/or mental illnesses.

The present invention also provides a method for the treatment of a non-human mammal or hum an requiring the treatment of medically relevant symptoms by administration of a therapeutically effective dose of a substituted 5,6,6a,11b-tetrahydro-7-oxa-5-aza-benzo[c]fluorene-6-carboxylic acid compound according to the invention of the formula I; in the form as prepared or in the form of the acid or base or in the form of the salts thereof, in particular the physiologically acceptable salts, or in the form of the solvates thereof, in particular the hydrates; in particular in the form of the physiologically acceptable salts thereof with cations or bases or with anions or acids; optionally in the form of the racemates thereof, the pure stereoisomers thereof, in particular enantiomers or diastereomers, or in the form of mixtures of the stereoisomers, in particular the enantiomers or diastereomers, in any desired mixing ratio; or of a pharmaceutical preparation according to the invention. The invention in particular relates to a corresponding method for the treatment of pain, in particular of neuropathic and/or chronic pain and/or for the treatment of migraine, for the treatment of urinary incontinence, pruritus, tinnitus and/or diarrhea, for the treatment/prevention of epilepsy, Parkinson's disease, Huntington's chorea, glaucoma, osteoporosis, ototoxicity, the withdrawal symptoms associated with alcohol and/or drug abuse, stroke, cerebral ischemia, cerebral infarcts, cerebral edema, hypoxia, anoxia and/or for anxiolysis and/or anesthesia or for the treatment/prevention of schizophrenia, Alzheimer's disease, psychoses due to increased amino acid levels, AIDS dementia, encephalomyelitis, Tourette's syndrome, perinatal asphyxia, inflammatory and allergic reactions, depression, drug and/or alcohol abuse, gastritis, diabetes, cardiovascular diseases, respiratory diseases, coughing and/or mental illnesses.

The following Examples are provided to illustrate the invention and are not intended to, nor should they be understood to be, limiting.

EXAMPLES

The following Examples illustrate compounds according to the invention and the preparation thereof and efficacy testing performed with said compounds.

The following general comments apply:

The chemicals and solvents used were purchased from conventional suppliers (Acros, Avocado, Aldrich, Fluka, Lancaster, Maybridge, Merck, Sigma, TCI etc.) or were synthesized by general production methods known to the person skilled in the art. In particular, some of the benzofurans, together with some others of the compounds used, were synthesized as synthesis building blocks using known synthetic methods prior to the basic synthesis described below. Thin-layer chromatography was performed with pre-coated silica gel 60 F 254 HPTLC plates from E. Merck, Darmstadt. The yields of the compounds produced are not optimized.

Analysis was performed by ESI mass spectroscopy.

The compounds are numbered, the value in brackets in principle corresponding to the number of the assigned compound.

Example 0

Basic Process a) One equivalent each of aniline compound and trifluoroacetic acid are dissolved in 6 ml/mmol of acetonitrile with stirring at room temperature, and then 1.1 equivalents of ethyl glyoxalate (50% in toluene) or 1.1 equivalents glyoxylic acid monohydrate are added. After ten minutes, 3 equivalents of the benzofuran component are added and the course of the reaction is monitored by thin-layer chromatography (mobile solvent system diethyl ether/hexane, 1:1). The reaction is complete after 2 hours (TLC monitoring). The reaction batch is combined with an excess of saturated aqueous sodium hydrogencarbonate solution and the organic phase is extracted three times with diethyl ether. The organic phase is washed to neutrality with water, dried over magnesium sulfate, filtered, washed with diethyl ether and, after evaporation, isolated by recrystallization or silica gel chromatography. The 5,6,6a,11b-tetrahydro-7-oxa-5-aza-benzo[c]fluorene-6-carboxylic acid esters are characterized by ESI mass spectrometry.

b) Optional subsequent preparation of the free 5,6,6a,11b-tetrahydro-7-oxa-5-aza-benzo[c]fluorene-6-carboxylic acids The above-described 5,6,6a,11b-tetrahydro-7-oxa-5-aza-benzo [c]fluorene-6-carboxylic acid ester (1 equivalent) is dissolved in 4 ml/mmol of ethanol and combined with 1.2 equivalents of aqueous 6N sodium hydroxide solution and stirred at room temperature. The course of the ester saponification is monitored by thin-layer chromatography (mobile solvent system diethyl ether/hexane, 1:1) and is complete after 30 minutes (TLC monitoring). The reaction mixture is evaporated in a rotary evaporator, redissolved in approximately 10 ml of water and adjusted to pH 1 with 32% HCl. The aqueous solution is extracted five times with diethyl ether and, after drying over magnesium sulfate, is evaporated.

Automated Method

A stirrer was placed in a round-bottomed glass tube (diameter 16 mm, length 125 mm) with a thread and the tube sealed using a screw lid with septum. The tube was placed in a stirring block, which had been adjusted to 20° C. The following reagents were then added in succession by pipette:

1 ml of a solution of trifluoroacetic acid, 0,1 M, and aniline component, 0.1 M, in acetonitrile;

1 ml of a 0.11 M solution of the aldehyde in acetonitrile;

1 ml of a 0.3 M solution of the benzofuran in acetonitrile.

In this connection, aldehyde should be taken to mean both the glyoxalic acid and the glyoxalic ester, preferably the alkyl ester, in particular the ethyl or methyl ester. The reaction mixture was stirred for 10 hours at 20° C. in one of the stirring blocks. The reaction solution was then filtered. The tube was then rinsed twice with 1.5 ml portions of a 7.5% $NaHCO_3$ solution.

The reaction mixture was combined with 2 ml of ethyl acetate on a vortexer and shaken. The mixture was briefly centrifuged to form a phase boundary. The phase boundary was detected optically and the organic phase removed by pipette. In the next step, the aqueous phase was again combined with 2 ml of ethyl acetate, shaken, centrifuged and the organic phase removed by pipette. The combined organic phases were dried over 2.4 g of $MgSO_4$ (pellets). The solvent was removed in a vacuum centrifuge.

The free 5,6,6a,11b-tetrahydro-7-oxa-5-aza-benzo[c]fluorene-6-carboxylic acid or ester was characterized by ESI mass spectrometry.

In principle, in the case of compounds with R3≠H, both the automated and the normal basic process may be followed by saponification in accordance with methods known to the person skilled in the art, such as for example with KOH solution or NaOH solution in methanol or ethanol at 0° C.–100° C., preferably at 40° C.–60° C.

Example 1

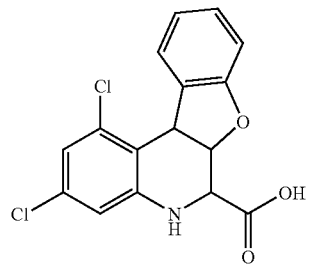

1,3-Dichloro-5,6,6a,11b-tetrahydro-7-oxa-5-aza-benzo [c]fluorene-6-carboxylic acid (1)

Compound 1 was produced in accordance with the basic process according to Example 0 from 3,5-dichloroaniline, glyoxalic acid ethyl ester and the unsubstituted benzofuran, the resultant ester subsequently being saponified.

Example 2

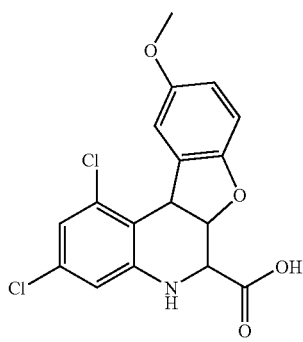

1,3-Dichloro-10-methoxy-5,6,6a,11b-tetrahydro-7-oxa-5-aza-benzo [c]fluorene-6-carboxylic acid (2)

Compound 2 was produced in accordance with the basic process according to Example 0 from 3,5-dichloroaniline, glyoxalic acid ethyl ester and 5-methoxybenzofuran, the resultant ester subsequently being saponified.

Example 3

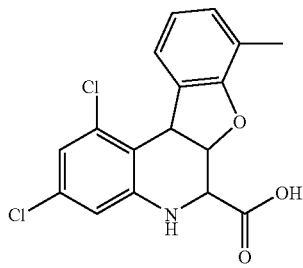

1,3-Dichloro-8-methyl-5,6,6a,11b-tetrahydro-7-oxa-5-aza-benzo [c]fluorene-6-carboxylic acid (3)

Compound 3 was produced in accordance with the basic process according to Example 0 from 3,5-dichloroaniline, glyoxalic acid ethyl ester and 7-methylbenzofuran, the resultant ester subsequently being saponified.

Example 4

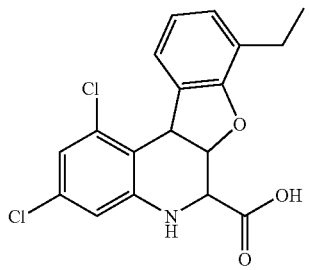

1,3-Dichloro-8-ethyl-5,6,6a,11b-tetrahydro-7-oxa-5-aza-benzo [c]fluorene-6-carboxylic acid (4)

Compound 4 was produced in accordance with the basic process according to Example 0 from 3,5-dichloroaniline, glyoxylic acid ethyl ester and 7-ethylbenzofuran, the resultant ether subsequently being saponified.

Example 5

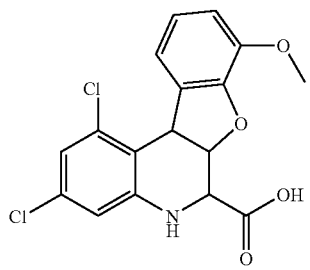

1,3-Dichloro-8-ethyl-5,6,6a,11b-tetrahydro-7-oxa-5-aza-benzo[c]fluorene-6-carboxylic acid (5)

Compound 5 was produced in accordance with the basic process according to Example 0 from 3,5-dichloroaniline, glyoxalic acid ethyl ester and 7-methoxybenzofuran, the resultant ester subsequently being saponified.

Example 6

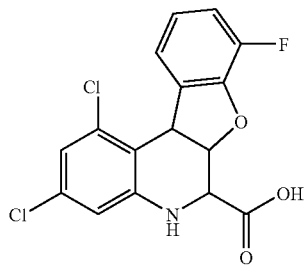

1,3-Dichloro-8-fluoro-5,6,6a,11b-tetrahydro-7-oxa-5-aza-benzo [c]fluorene-6-carboxylic acid (6)

Compound 6 was produced in accordance with the basic process according to Example 0 from 3,5-dichloroaniline, glyoxalic acid ethyl ester and 7-fluorobenzofuran, the resultant ester subsequently being saponified.

Example 7

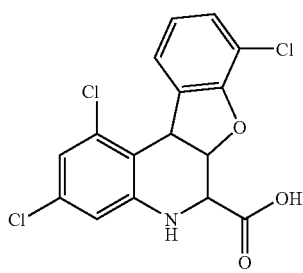

1,3,8-Trichloro-5,6,6a,11b-tetrahydro-7-oxa-5-aza-benzo [c]fluorene-6-carboxylic acid (7)

Compound 7 was produced in accordance with the basic process according to Example 0 from 3,5-dichloroaniline, glyoxalic acid ethyl ester and 7-chlorobenzofuran, the resultant ester subsequently being saponified.

Example 8

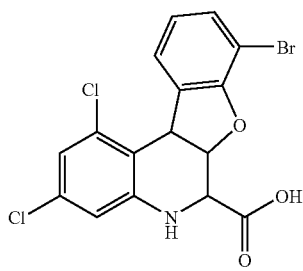

8-Bromo-1,3-dichloro-5,6,6a,11b-tetrahydro-7-oxa-5-aza-benzo [c]fluorene-6-carboxylic acid (8)

Compound 8 was produced in accordance with the basic process according to Example 0 from 3,5-dichloroaniline, glyoxalic acid ethyl ester and 7-bromobenzofuran, the resultant ester subsequently being saponified.

Example 9

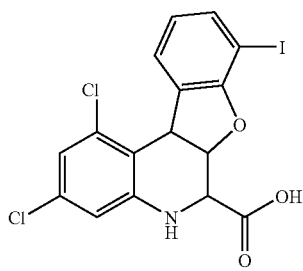

8-Iodo-1,3-dichloro-5,6,6a,11b-tetrahydro-7-oxa-5-aza-benzo [c]fluorene-6-carboxylic acid (9)

Compound 9 was produced in accordance with the basic process according to Example 0 from 3,5-dichloroaniline, glyoxalic acid ethyl ester and 7-iodobenzofuran, the resultant ester subsequently being saponified.

Example 10

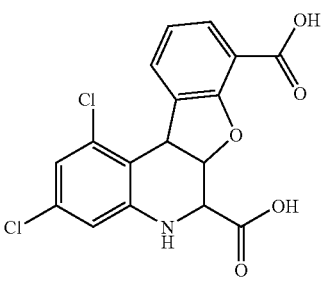

1,3-Dichloro-5,6,6a,11b-tetrahydro-7-oxa-5-aza-benzo [c]fluorene-6,8-dicarboxylic acid (10)

Compound 10 was produced in accordance with the basic process according to Example 0 from 3,5-dichloroaniline, glyoxalic acid ethyl ester and benzofuran-7-carboxylic acid, the resultant ester subsequently being saponified.

Example 11

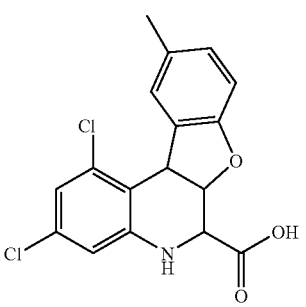

1,3-Dichloro-10-methyl-5,6,6a,11b-tetrahydro-7-oxa-5-aza-benzo [c]fluorene-6-carboxylic acid (11)

Compound 11 was produced in accordance with the basic process according to Example 0 from 3,5-dichloroaniline, glyoxalic acid ethyl ester and 5-methylbenzofuran, the resultant ester subsequently being saponified.

Example 12

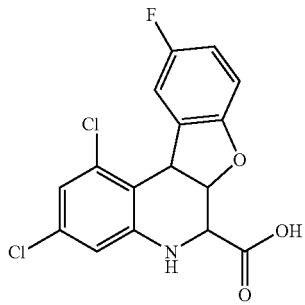

1,3-Dichloro-10-fluoro-5,6,6a,11b-tetrahydro-7-oxa-5-aza-benzo [c]fluorene-6-carboxylic acid (12)

Compound 12 was produced in accordance with the basic process according to Example 0 from 3,5-dichloroaniline, glyoxalic acid ethyl ester and 5-fluorobenzofuran, the resultant ester subsequently being saponified.

Example 13

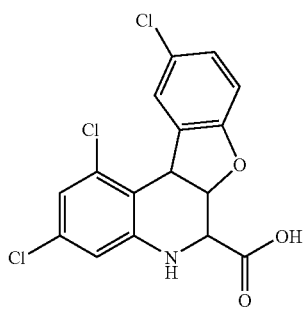

1,3,10-Trichloro-5,6,6a,11b-tetrahydro-7-oxa-5-aza-benzo [c]fluorene-6-carboxylic acid (13)

Compound 13 was produced in accordance with the basic process according to Example 0 from 3,5-dichloroaniline, glyoxalic acid ethyl ester and 5-chlorobenzofuran, the resultant ester subsequently being saponified.

Example 14

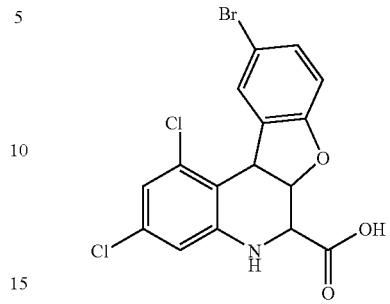

10-Bromo-1,3-dichloro-5,6,6a,11b-tetrahydro-7-oxa-5-aza-benzo [c]fluorene-6-carboxylic acid (14)

Compound 14 was produced in accordance with the basic process according to Example 0 from 3,5-dichloroaniline, glyoxalic acid ethyl ester and 5-bromobenzofuran, the resultant ester subsequently being saponified.

Example 15

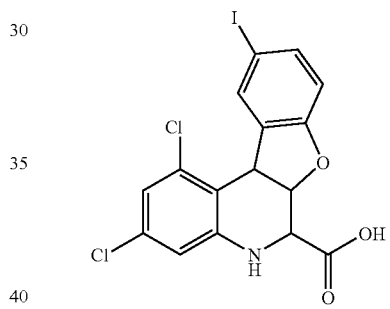

10-Iodo-1,3-dichloro-5,6,6a,11b-tetrahydro-7-oxa-5-aza-benzo [c]fluorene-6-carboxylic acid (15)

Compound 15 was produced in accordance with the basic process according to Example 0 from 3,5-dichloroaniline, glyoxalic acid ethyl ester and 5-iodobenzofuran, the resultant ester subsequently being saponified.

Example 16

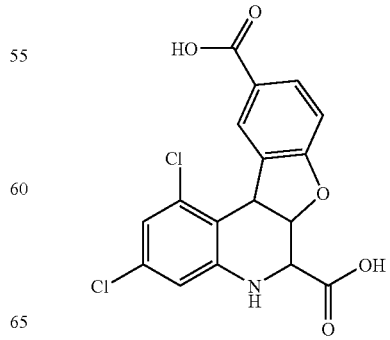

1,3-Dichloro-5,6,6a,11b-tetrahydro-7-oxa-5-aza-benzo [c]fluorene-6,10-dicarboxylic acid (16)

Compound 16 was produced in accordance with the basic process according to Example 0 from 3,5-dichloroaniline, glyoxalic acid ethyl ester and benzofuran-5-carboxylic acid, the resultant ester subsequently being saponified.

Example 17

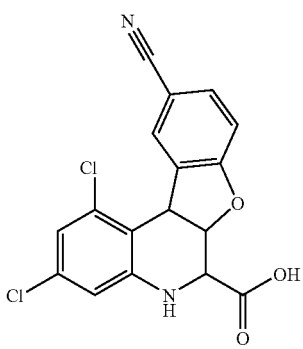

1,3-Dichloro-10-cyano-5,6,6a,11b-tetrahydro-7-oxa-5-aza-benzo [c]fluorene-6-carboxylic acid (17)

Compound 17 was produced in accordance with the basic process according to Example 0 from 3,5-dichloroaniline, glyoxalic acid ethyl ester and 5-cyanobenzofuran, the resultant ester subsequently being saponified.

Example 18

General Preparation of the Salts with Cations by Way of Example of the Compounds According to Examples 1–17

One equivalent of the compound according to one of Examples 1 to 17, preferably an imino acid, is suspended in a little water and one equivalent of 1 normal aqueous alkali solution, preferably NaOH or KOH, is added. If solubility is poor, methanol is added dropwise until complete dissolution is achieved. After 30 minutes' stirring at room temperature, the mixture is evaporated in a rotary evaporator, the remaining solution is frozen at –60° C. in a mixture of isopropanol/dry ice and freeze-dried. The salts, in particular of the imino acids, preferably the sodium or potassium salts, are obtained as generally colorless solids.

Alternatively, it is also possible to produce the potassium or sodium salts with potassium or sodium trimethylsilanolate (E. D. Laganis, B. L. Chenard; Tetrahedron Letters 25, 5831–5834 (1984)). Potassium or sodium trimethylsilanolate is dissolved under nitrogen in an organic solvent (for instance, dichloromethane, toluene or THF) and the ester or acid is added in a single portion. The reaction mixture is stirred for four hours at room temperature and filtered. The generally colorless solid is washed with diethyl ether and dried under a vacuum. The potassium or sodium salts are obtained as solids.

The compounds according to Example 19 to 35 are sodium salts, produced in accordance with these example instructions, of compounds 1 to 17, while the compounds according to Examples 36 to 52 are the correspondingly produced potassium salts.

Example 19

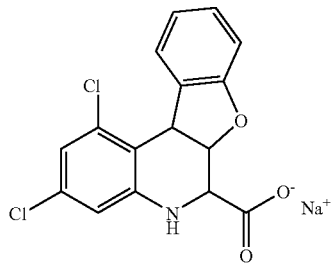

1,3-Dichloro-5,6,6a,11b-tetrahydro-7-oxa-5-aza-benzo[c]fluorene-6-carboxylate; sodium salt (19)

Compound 19 was produced by the process according to Example 18 from compound 1.

Example 20

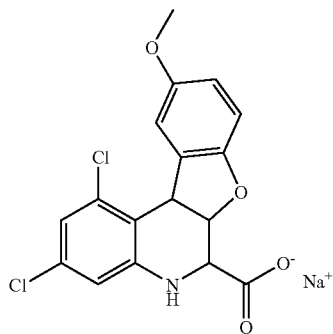

1,3-Dichloro-10-methoxy-5,6,6a,11b-tetrahydro-7-oxa-5-aza-benzo [c]fluorene-6-carboxylate; sodium salt (20)

Compound 20 was produced by the process according to Example 18 from compound 2.

Example 21

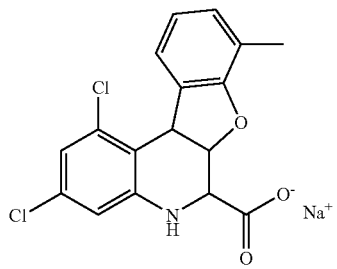

1,3-Dichloro-8-methyl-5,6,6a,11b-tetrahydro-7-oxa-
5-aza-benzo [c]fluorene-6-carboxylate; sodium salt
(21)

Compound 21 was produced by the process according to Example 18 from compound 3.

Example 22

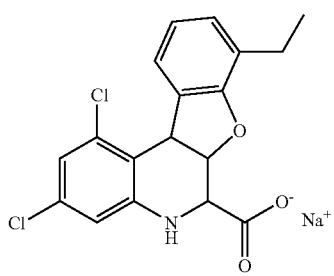

1,3-Dichloro-8-ethyl-5,6,6a,11b-tetrahydro-7-oxa-5-
aza-benzo [c]fluorene-6-carboxylate; sodium salt
(22)

Compound 22 was produced by the process according to Example 18 from compound 4.

Example 23

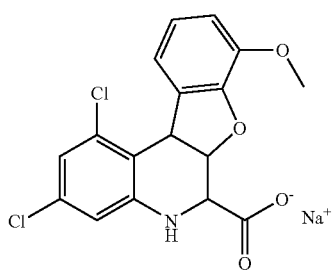

1,3-Dichloro-8-ethyl-5,6,6a,11b-tetrahydro-7-oxa-5-
aza-benzo[c]fluorene-6-carboxylate; sodium salt
(23)

Compound 23 was produced by the process according to Example 18 from compound 5.

Example 24

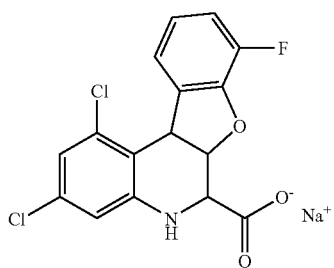

1,3-Dichloro-8-fluoro-5,6,6a,11b-tetrahydro-7-oxa-
5-aza-benzo [c]fluorene-6-carboxylate; sodium salt
(24)

Compound 24 was produced by the process according to Example 18 from compound 6.

Example 25

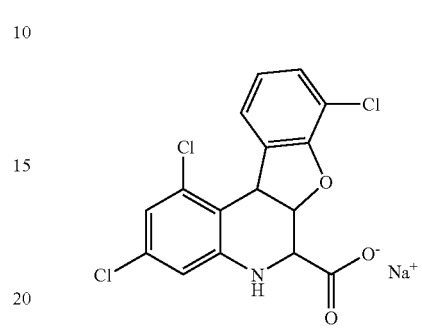

1,3,8-Trichloro-5,6,6a,11b-tetrahydro-7-oxa-5-aza-
benzo [c]fluorene-6-carboxylate; sodium salt (25)

Compound 25 was produced by the process according to Example 18 from compound 7.

Example 26

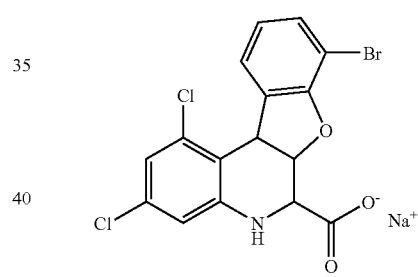

8-Bromo-1,3-dichloro-5,6,6a,11b-tetrahydro-7-oxa-
5-aza-benzo[c]fluorene-6-carboxylate; sodium salt
(26)

Compound 26 was produced by the process according to Example 18 from compound 8.

Example 27

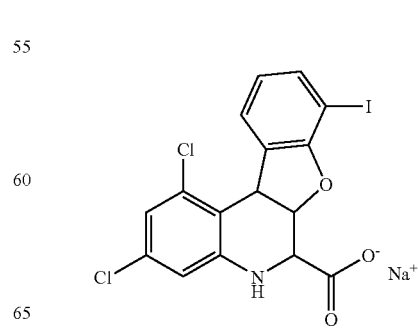

8-Iodo-1,3-dichloro-5,6,6a,11b-tetrahydro-7-oxa-5-aza-benzo [c]fluorene-6-carboxylate; sodium salt (27)

Compound 27 was produced by the process according to Example 18 from compound 9.

Example 28

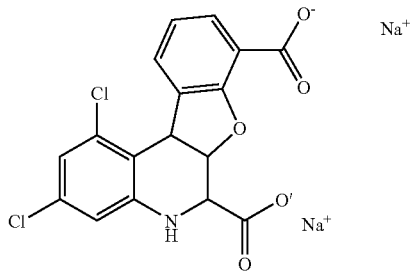

1,3-Dichloro-5,6,6a,11b-tetrahydro-7-oxa-5-aza-benzo [c]fluorene-6,8-dicarboxylate; disodium salt (28)

Compound 28 was produced by the process according to Example 18 from compound 10.

Example 29

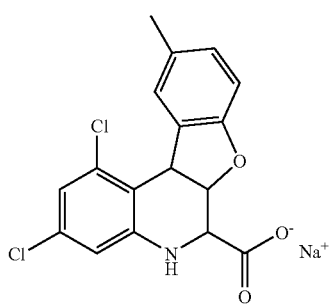

1,3-Dichloro-10-methyl-5,6,6a,11b-tetrahydro-7-oxa-5-aza-benzo [c]fluorene-6-carboxylate; sodium salt (29)

Compound 29 was produced by the process according to Example 18 from compound 11.

Example 30

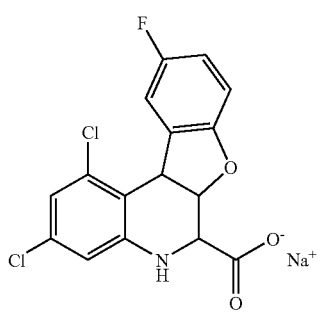

1,3-Dichloro-10-fluoro-5,6,6a,11b-tetrahydro-7-oxa-5-aza-benzo [c]fluorene-6-carboxylate; sodium salt (30)

Compound 30 was produced by the process according to Example 18 from compound 12.

Example 31

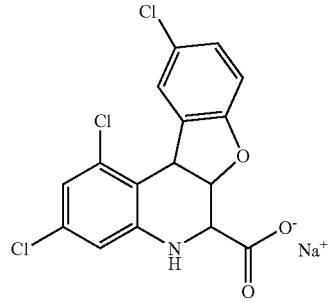

1,3,10-Trichloro-5,6,6a,11b-tetrahydro-7-oxa-5-aza-benzo[c]fluorene-6-carboxylate; sodium salt (31)

Compound 31 was produced by the process according to Example 18 from compound 13.

Example 32

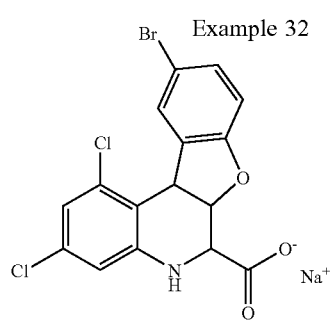

10-Bromo-1,3-dichloro-5,6,6a,11b-tetrahydro-7-oxa-5-aza-benzo[c]fluorene-6-carboxylate; sodium salt (32)

Compound 32 was produced by the process according to Example 18 from compound 14.

Example 33

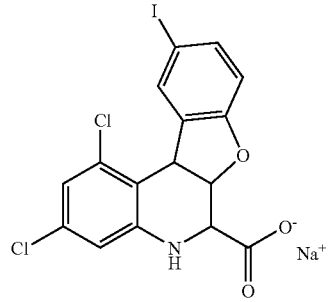

10-Iodo-1,3-dichloro-5,6,6a,11b-tetrahydro-7-oxa-5-aza-benzo [c]fluorene-6-carboxylate; sodium salt (33)

Compound 33 was produced by the process according to Example 18 from compound 15.

Example 34

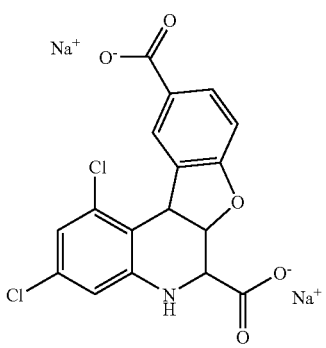

1,3-Dichloro-5,6,6a,11b-tetrahydro-7-oxa-5-aza-benzo[c]fluorene-6,10-dicarboxylate; disodium salt (34)

Compound 34 was produced by the process according to Example 18 from compound 16.

Example 35

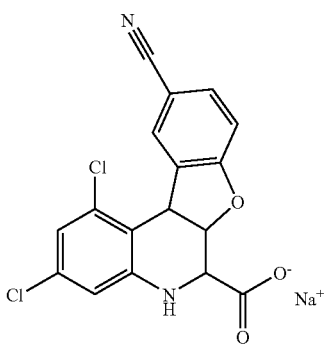

1,3-Dichloro-10-cyano-5,6,6a,11b-tetrahydro-7-oxa-5-aza-benzo [c]fluorene-6-carboxylate; sodium salt (35)

Compound 35 was produced by the process according to Example 18 from compound 17.

Example 36

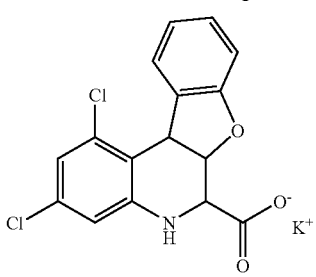

1,3-dichloro-5,6,6a,11b-tetrahydro-7-oxa-5-aza-benzo [c]fluorene-6-carboxylate; potassium salt (36)

Compound 36 was produced by the process according to Example 18 from compound 1.

Example 37

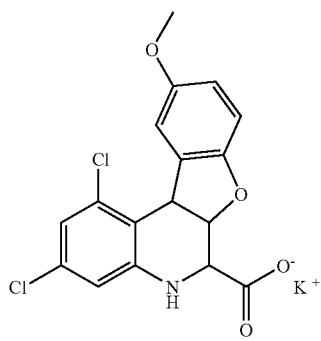

1,3-Dichloro-10-methoxy-5,6,6a,11b-tetrahydro-7-oxa-5-aza-benzo [c]fluorene-6-carboxylate; potassium salt (37)

Compound 37 was produced by the process according to Example 18 from compound 2.

Example 38

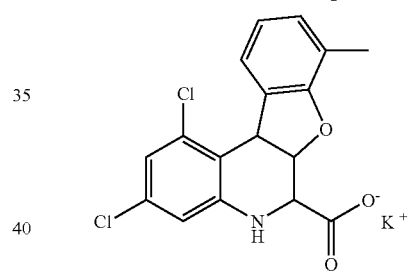

1,3-Dichloro-8-methyl-5,6,6a,11b-tetrahydro-7-oxa-5-aza-benzo [c]fluorene-6-carboxylate; potassium salt (38)

Compound 38 was produced by the process according to Example 18 from compound 3.

Example 39

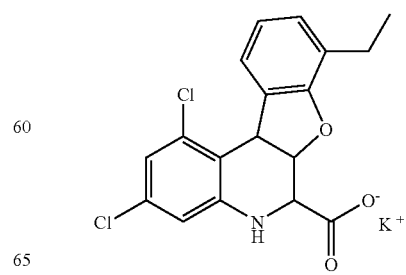

1,3-Dichloro-8-ethyl-5,6,6a,11b-tetrahydro-7-oxa-5-aza-benzo [c]fluorene-6-carboxylate potassium salt (39)

Compound 39 was produced by the process according to Example 18 from compound 4.

Example 40

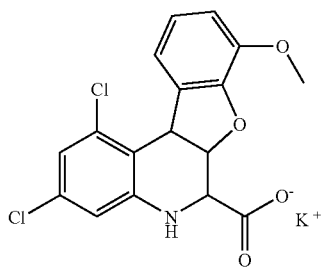

1,3-Dichloro-8-ethyl-5,6,6a,11b-tetrahydro-7-oxa-5-aza-benzo[c]fluorene-6-carboxylate potassium salt (40)

Compound 40 was produced by the process according to Example 18 from compound 5.

Example 41

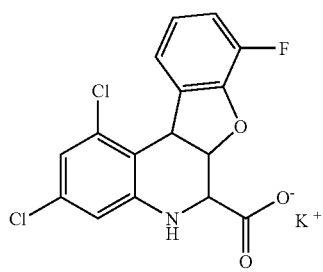

1,3-Dichloro-8-fluoro-5,6,6a,11b-tetrahydro-7-oxa-5-aza-benzo [c]fluorene-6-carboxylate; potassium salt (41)

Compound 41 was produced by the process according to Example 18 from compound 6.

Example 42

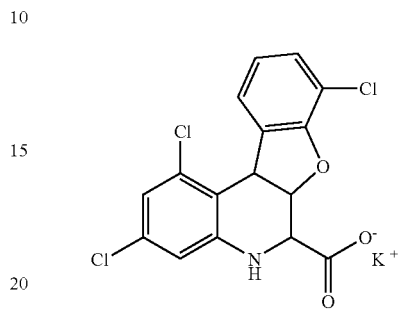

1,3,8-Trichloro-5,6,6a,11b-tetrahydro-7-oxa-5-aza-benzo [c]fluorene-6-carboxylate; potassium salt (42)

Compound 42 was produced by the process according to Example 18 from compound 7.

Example 43

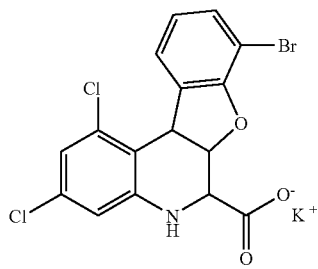

8-Bromo-1,3-dichloro-5,6,6a,11b-tetrahydro-7-oxa-5-aza-benzo [c]fluorene-6-carboxylate; potassium salt (43)

Compound 43 was produced by the process according to Example 18 from compound 8.

Example 44

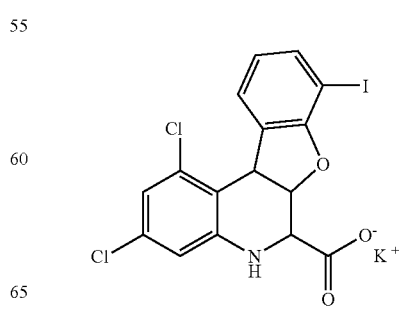

8-Iodo-1,3-dichloro-5,6,6a,11b-tetrahydro-7-oxa-5-aza-benzo [c]fluorene-6-carboxylate; potassium salt (44)

Compound 44 was produced by the process according to Example 18 from compound 9.

Example 45

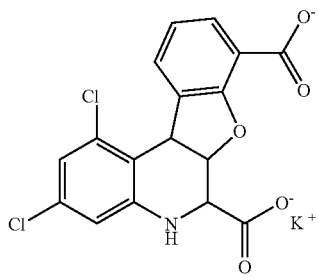

1,3-Dichloro-5,6,6a,11b-tetrahydro-7-oxa-5-aza-benzo [c]fluorene-6,8-dicarboxylate; dipotassium salt (45)

Compound 45 was produced by the process according to Example 18 from compound 10.

Example 46

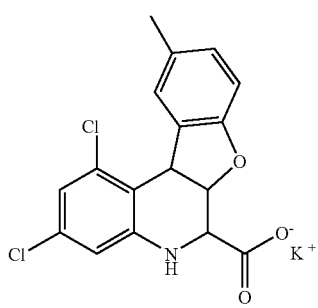

1,3-Dichloro-10-methyl-5,6,6a,11b-tetrahydro-7-oxa-5-aza-benzo [c]fluorene-6-carboxylate; potassium salt (46)

Compound 46 was produced by the process according to Example 18 from compound 11.

Example 47

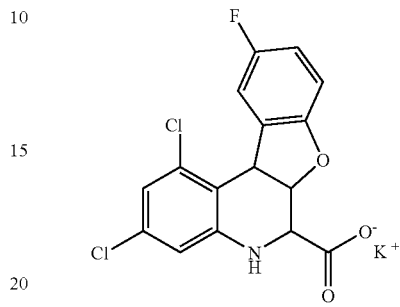

1,3-Dichloro-10-fluoro-5,6,6a,11b-tetrahydro-7-oxa-5-aza-benzo [c]fluorene-6-carboxylate; potassium salt (47)

Compound 47 was produced by the process according to Example 18 from compound 12.

Example 48

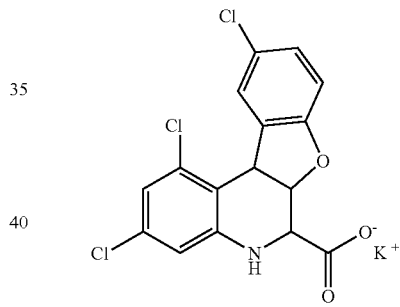

1,3,10-Trichloro-5,6,6a,11b-tetrahydro-7-oxa-5-aza-benzo[c]fluorene-6-carboxylate; potassium salt (48)

Compound 31 was produced by the process according to Example 18 from compound 13.

Example 49

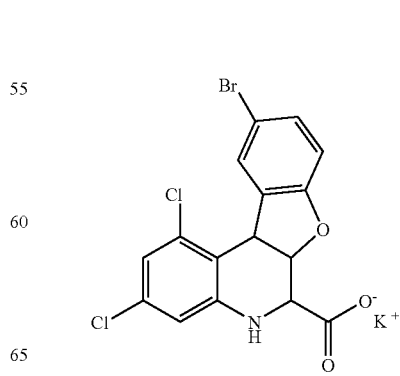

10-Bromo-1,3-dichloro-5,6,6a,11b-tetrahydro-7-oxa-5-aza-benzo [c]fluorene-6-carboxylate; potassium salt (49)

Compound 49 was produced by the process according to Example 18 from compound 14.

Example 50

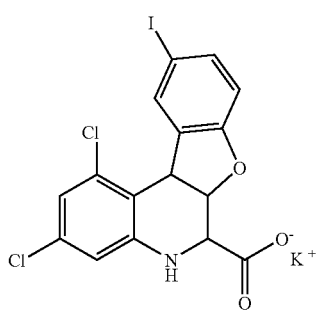

10-Iodo-1,3-dichloro-5,6,6a,11b-tetrahydro-7-oxa-5-aza-benzo [c]fluorene-6-carboxylate; potassium salt (50)

Compound 50 was produced by the process according to Example 18 from compound 15.

Example 51

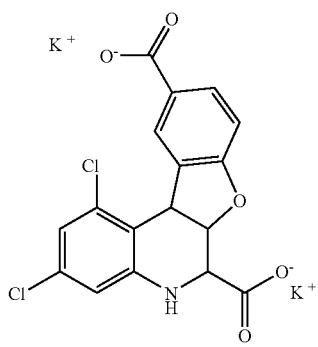

1,3-Dichloro-5,6,6a,11b-tetrahydro-7-oxa-5-aza-benzo[c]fluorene-6,10-dicarboxylate; dipotassium salt (51)

Compound 51 was produced by the process according to Example 18 from compound 16.

Example 52

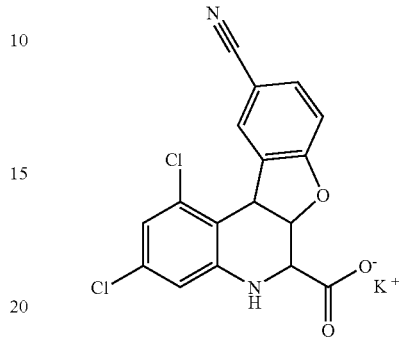

1,3-Dichloro-10-cyano-5,6,6a,11b-tetrahydro-7-oxa-5-aza-benzo[c]fluorene-6-carboxylate; potassium salt (52)

Compound 52 was produced by the process according to Example 18 from compound 17.

Example 53

General Preparation of the Salts with Anions by Way of Example of the Hydrochloride Salt of the Compounds According to Examples 1–17

One equivalent of the compound according to one of Examples 1 to 17 is dissolved in approximately 10 ml of 2-butanone per gram of substance. Half a mol equivalent of water is then added, followed by 1.1 mol equivalents of chlorotrimethylsilane. Then the mixture is stirred overnight. If no hydrochloride was formed on cooling to approximately 4° C., the precipitation batch was resuspended in twice the volume of water, washed with three small portions of ether, the aqueous phase was alkalized with a small volume of approximately 30% sodium hydroxide solution and extracted three times with ether ("acid-base extraction"). These final extracts were in turn combined and subjected to another hydrochloride precipitation.

The compounds according to Examples 54 to 70 are the hydrochloride salts, produced in accordance with these example instructions, of compounds 1 to

Example 54

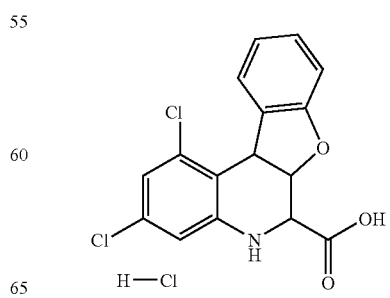

1,3-Dichloro-5,6,6a,11b-tetrahydro-7-oxa-5-aza-benzo[c]fluorene-6-carboxylic acid; hydrochloride salt (54)

Compound 54 was produced by the process according to Example 53 from compound 1.

Example 55

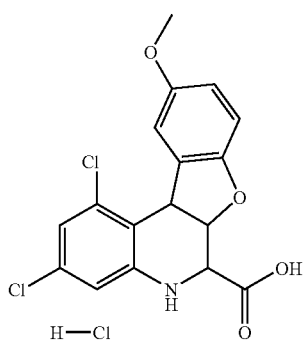

1,3-Dichloro-10-methoxy-5,6,6a,11b-tetrahydro-7-oxa-5-aza-benzo[c]fluorene-6-carboxylic acid; hydrochloride salt (55)

Compound 55 was produced by the process according to Example 53 from compound 2.

Example 56

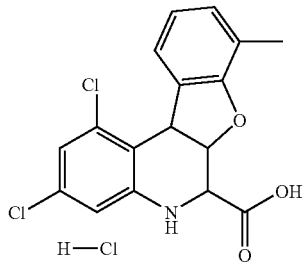

1,3-Dichloro-8-methyl-5,6,6a,11b-tetrahydro-7-oxa-5-aza-benzo[c]fluorene-6-carboxylic acid; hydrochloride salt (56)

Compound 56 was produced by the process according to Example 53 from compound 3.

Example 57

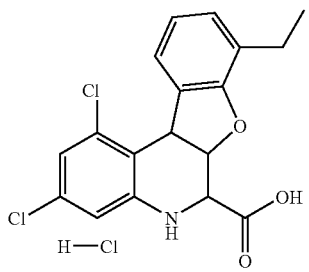

1,3-Dichloro-8-ethyl-5,6,6a,11b-tetrahydro-7-oxa-5-aza-benzo[c]fluorene-6-carboxylic acid; hydrochloride salt (57)

Compound 57 was produced by the process according to Example 53 from compound 4.

Example 58

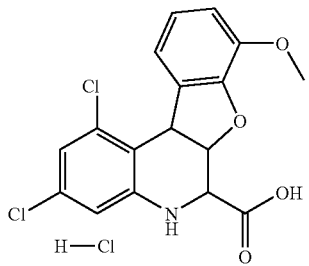

1,3-Dichloro-8-ethyl-5,6,6a,11b-tetrahydro-7-oxa-5-aza-benzo[c]fluorene-6-carboxylic acid; hydrochloride salt (58)

Compound 58 was produced by the process according to Example 53 from compound 5.

Example 59

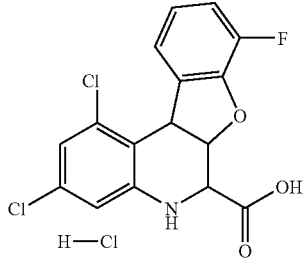

1,3-Dichloro-8-fluoro-5,6,6a,11b-tetrahydro-7-oxa-5-aza-benzo [c]fluorene-6-carboxylic acid; hydrochloride salt (59)

Compound 59 was produced by the process according to Example 53 from compound 6.

Example 60

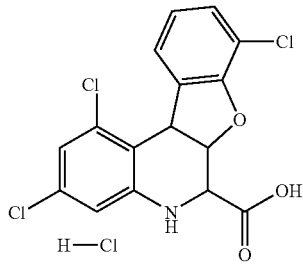

1,3,8-Trichloro-5,6,6a,11b-tetrahydro-7-oxa-5-aza-benzo [c]fluorene-6-carboxylic acid; hydrochloride salt (60)

Compound 60 was produced by the process according to Example 53 from compound 7.

Example 61

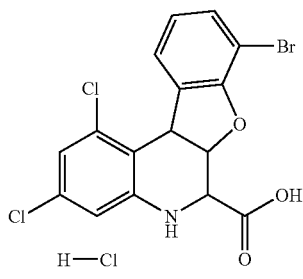

8-Bromo-1,3-dichloro-5,6,6a,11b-tetrahydro-7-oxa-5-aza-benzo [c]fluorene-6-carboxylic acid; hydrochloride salt (61)

Compound 61 was produced by the process according to Example 53 from compound 8.

Example 62

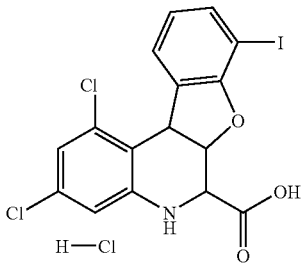

8-Iodo-1,3-dichloro-5,6,6a,11b-tetrahydro-7-oxa-5-aza-benzo [c]fluorene-6-carboxylic acid; hydrochloride salt (62)

Compound 62 was produced by the process according to Example 53 from compound 9.

Example 63

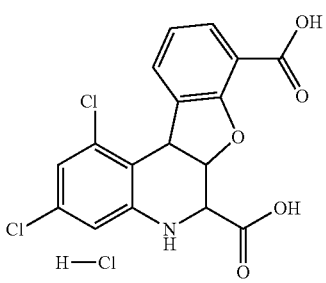

1,3-Dichloro-5,6,6a,11b-tetrahydro-7-oxa-5-aza-benzo [c]fluorene-6,8-dicarboxylic acid; hydrochloride salt (63)

Compound 63 was produced by the process according to Example 53 from compound 10.

Example 64

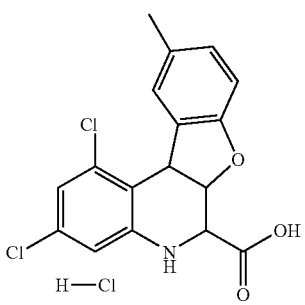

1,3-Dichloro-10-methyl-5,6,6a,11b-tetrahydro-7-oxa-5-aza-benzo [c]fluorene-6-carboxylic acid; hydrochloride salt (64)

Compound 64 was produced by the process according to Example 53 from compound 11.

Example 65

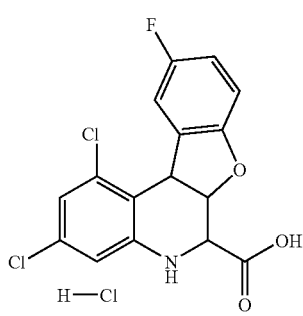

1,3-Dichloro-10-fluoro-5,6,6a,11b-tetrahydro-7-oxa-5-aza-benzo[c]fluorene-6-carboxylic acid; hydrochloride salt (65)

Compound 65 was produced by the process according to Example 53 from compound 12.

Example 66

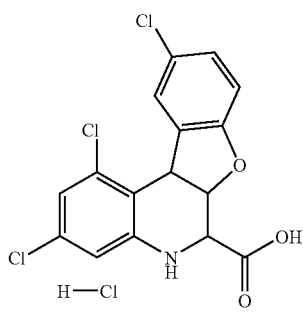

1,3,10-Trichloro-5,6,6a,11b-tetrahydro-7-oxa-5-aza-benzo [c]fluorene-6-carboxylic acid; hydrochloride salt (66)

Compound 66 was produced by the process according to Example 53 from compound 13.

Example 67

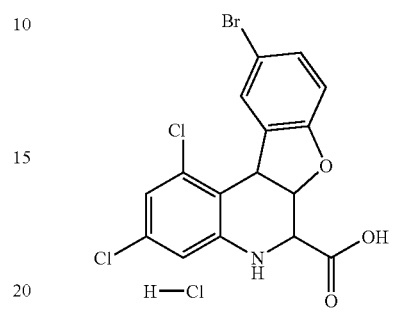

10-Bromo-1,3-dichloro-5,6,6a,11b-tetrahydro-7-oxa-5-aza-benzo[c]fluorene-6-carboxylic acid; hydrochloride salt (67)

Compound 67 was produced by the process according to Example 53 from compound 14.

Example 68

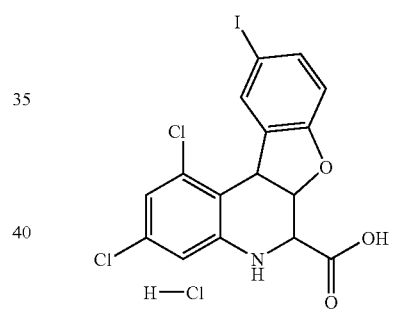

10-Iodo-1,3-dichloro-5,6,6a,11b-tetrahydro-7-oxa-5-aza-benzo[c]fluorene-6-carboxylic acid; hydrochloride salt (68)

Compound 68 was produced by the process according to Example 53 from compound 15.

Example 69

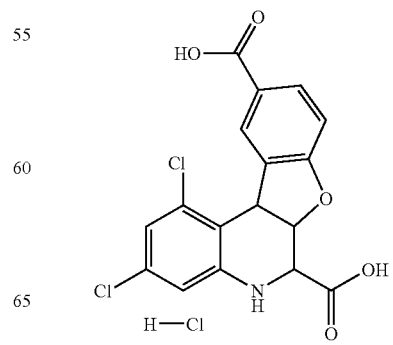

1,3-Dichloro-5,6,6a,11b-tetrahydro-7-oxa-5-aza-benzo [c]fluorene-6,10-dicarboxylic acid; hydrochloride salt (69)

Compound 69 was produced by the process according to Example 53 from compound 16.

Example 70

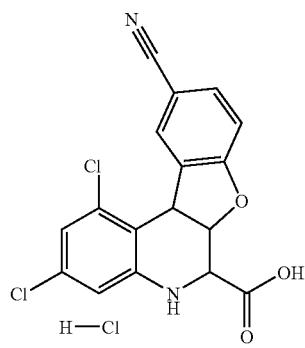

1,3-Dichloro-10-cyano-5,6,6a,11b-tetrahydro-7-oxa-5-aza-benzo [c]fluorene-6-carboxylic acid; hydrochloride salt (70)

Compound 70 was produced by the process according to Example 53 from compound 17.

Example 71

Receptor Binding (Glycine-Binding Site of the NMDA Receptor Channel)

The investigation for determining the affinity of the compounds according to the invention of the formula I towards the glycine-binding site of the NMDA receptor channel was performed on brain membrane homogenates (homogenate of the cortex and hippocampus area from male rat brain, Wistar strain) [B. M. Baron, B. W. Siegel, B. L. Harrison, R. S. Gross, C. Hawes and P. Towers, Journal of Pharmacology and Experimental Therapeutics, vol. 279, p. 62, 1996].

To this end, the cortex and hippocampus were dissected out of freshly harvested rat brains and homogenized with ice cooling in 5 mmol/l of TRIS-acetate buffer, 0.32 mol/l of sucrose, pH 7.4 (10 ml/g fresh weight) using a Potter homogenizer (Braun/Melsungen, 10 piston strokes at 500 rpm) and then centrifuged for 10 minutes at 1,000 g and 4° C. The first supernatant was collected and the sediment again homogenized with ice cooling with 5 mmol/l of TRIS-acetate buffer, 0.32 mol/l of sucrose, pH 7.4 (5 ml/g of original fresh weight) with the Potter homogenizer (10 piston strokes at 500 rpm) and centrifuged for 10 minutes at 1,000 g and 4° C. The resultant supernatant was combined with the supernatant from the first centrifugation and centrifuged at 17,000 g for 20 minutes at 4° C. The supernatant after this centrifugation was discarded and the membrane sediment was resuspended with 5 mmol/l of TRIS-acetate buffer, pH 8.0 (20 ml/g of original fresh weight) and homogenized with 10 piston strokes at 500 rpm. The membrane homogenate was then incubated for 1 hour at 4° C. and centrifuged for 30 minutes at 50,000 g and 4° C. The supernatant was discarded and the centrifuge tubes containing the membrane sediment were sealed with Parafilm and frozen for 24 hours at −20° C. On the following day, the membrane sediment was thawed and resuspended with ice-cold 5 mmol/l TRIS-acetate buffer, 0.1% saponin (wt./vol.), pH 7.0 (10 ml/g of original fresh weight) and homogenized with 10 piston strokes at 500 rpm and then centrifuged for 20 minutes at 50,000 g and 4° C. The resultant supernatant was discarded and the sediment resuspended in a small volume with 5 mmol/l of TRIS-acetate buffer, pH 7.0 (approximately 2 ml/g of original fresh weight) redissolved and again homogenized with 10 piston strokes at 500 rpm. After determination of the protein content, the membrane homogenate was adjusted with 5 mmol/l TRIS-acetate buffer, pH 7.0, to a protein concentration of 10 mg of protein/ml and frozen in aliquots until used for testing. The receptor binding test was performed by thawing aliquots, diluting them 1:10 with 5 mmol/l TRIS-acetate buffer, pH 7.0, homogenizing them with ice-cooling with 10 piston strokes at 500 rpm with the Potter homogenizer (10 piston strokes at 500 rpm) and centrifuging them for 60 minutes at 55,000 g at 4° C. The supernatant was decanted and the membrane sediment adjusted with ice-cold 50 mmol/l TRIS-acetate buffer, pH 7.0, to a protein concentration of 1 mg/ml and again homogenized with 10 piston strokes at 500 rpm and kept in suspension in an ice bath with stirring on a magnetic stirrer. This membrane homogenate was used in the receptor binding test in a quantity of 100 μl per 1 ml batch (0.1 mg of protein/ml in the final batch). In the binding test, the buffer used was 50 mmol/l TRIS-acetate buffer, pH 7.0, and the radioactive ligand was 1 nmol/l of ($^3$H)-MDL 105.519 (B. M. Baron et al. 1996). The level of non-specific binding was determined in the presence of 1 mmol/l of glycine.

In further batches, the compounds according to the invention were added in concentration series and the displacement of the radioactive ligand from its specific binding at the glycine-binding site of the NMDA receptor channel was determined. Each of the triplicate batches was incubated for 120 minutes at 4° C. and then harvested by filtration through glass fiber filter mats (GF/B) in order to determine the radioactivity bound to the membrane homogenate. The radioactivity retained on the glass fiber filters was measured in the β counter by addition of scintillating material.

The affinity of the compounds according to the invention towards the glycine-binding site of the NMDA receptor channel was calculated as an $IC_{50}$ value (concentration with 50% displacement of the radioactive ligand from its specific binding site) in accordance with the mass-action law by means of nonlinear regression and is stated in Table 1 after conversion (using the Cheng-Prussoff equation) as a Ki value (mean of three independent tests) or as the percentage of the previously bound radioactive ligand (see above) which is displaced from its specific binding site at a concentration of 10 μmol/l of the substance according to the invention under test.

TABLE 1

| | Glycine-binding site of the NMDA receptor channel | |
| --- | --- | --- |
| Example | Ki (μmol/l) | Displacement (%, 10 μmol/l) |
| 1 | 0.053 | 100 |

Example 72

Formaldehyde Test, Rat

The investigations to determine the antinociceptive action of the compounds according to the invention of the formula I were carried by the formaldehyde test on male rats (Sprague-Dawley, 150–170 g). In the formaldehyde test, a distinction is drawn between the first (early) phase (0–15 min after formaldehyde injection) and the second (later) phase (15–60 min after formaldehyde injection) (D. Dubuisson, S. G. Dennis, Pain 4, 161–174 (1977)). The early phase, being a direct response to the formaldehyde injection, is considered to be a model for acute pain, while the late phase is considered to be a model for persistent (chronic) pain (T. J. Coderre, J. Katz, A. L. Vaccarino, R. Melzack, Pain, Vol. 52, p. 259, 1993). The compounds according to the invention were investigated in the second phase of the formaldehyde test in order to obtain information concerning the effects of the substances in chronic/inflammatory pain.

A nociceptive reaction was induced in the freely mobile test animals by a single, subcutaneous formaldehyde injection (50 μl, 5%) into the dorsal side of the rear hind paw, the reaction being classed according to one of the following behavioral parameters: lifting and holding up the affected paw (score 1), shaking or twitching (score 2), licking and biting (score 3). The differential behavior induced by the formaldehyde injection was recorded by observing the animals in the late phase of the formaldehyde test and assigned a variable weighting in the evaluation. Normal behavior, in which the animal places an even load on all four paws, was recorded as a score of 0. The time of administration before the formaldehyde injection was selected as a function on the mode of administration of the compounds according to the invention (intraperitoneal: 15 min; intravenous: 5 min). After injection of the substances, which are antinociceptively active in the formaldehyde test, the described behaviors (score 1–3) of the animals are reduced or even eliminated. A comparison was made with control animals which had received vehicle (solvent) before administration of the formaldehyde. The nociceptive behavior was calculated as a "pain rate" (PR). The various behavioral parameters were differently weighted (factor of 0, 1, 2, 3). The calculation was carried out in accordance with the following equation at sub-intervals of 3 min:

$$PR=[(T_0\times0)+(T_1\times1)+(T_2\times2)+(T_3\times3)]/180,$$

wherein $T_0$, $T_1$, $T_2$, and $T_3$ in each case correspond to the time in seconds for which the animal exhibited behavior 0, 1, 2 or 3. Substance and vehicle groups in each case comprises n=10 animals. On the basis of the calculated PR values, the effect of the substance was determined as a percentage change relative to the control. The $ED_{50}$ calculations were carried out by regression analysis. All the compounds according to the invention exhibited moderate to strong inhibition of the formaldehyde-induced nociception.

The following Table summarizes the results from selected investigations in the rat formaldehyde test.

TABLE 2

| Compound | Mode of administration | $ED_{50}$ |
|---|---|---|
| 1 | i.v. | 7.27 mg/kg |

Example 73

Parenteral Administration Form 38.5 g of compound 1 were dissolved in 1 l of water for injection at room temperature and then adjusted to isotonic conditions by addition of anhydrous glucose for injection.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

What is claimed is:

1. A 5,6,6a,11b-tetrahydro-7-oxa-5-aza-benzo[c]fluorene-6-carboxylic acid compound corresponding to formula I

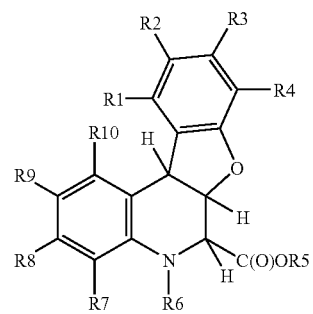

wherein $R^1$, $R^2$, $R^3$ and $R^4$ independently represent

H, F, Cl, Br, I, CN, $NO_2$; $C_1$–$C_{18}$ alkyl, $C_2$–$C_{18}$ alkenyl or $C_2$–$C_{18}$ alkynyl, in each case branched or unbranched, mono- or polysubstituted or unsubstituted; $C_3$–$C_8$ cycloalkyl, saturated or unsaturated, mono- or polysubstituted or unsubstituted, or a corresponding heterocycle, in which at least one C atom in the ring is replaced by N, S or O; alkylaryl or alkylheteroaryl, in each case mono- or polysubstituted or unsubstituted; aryl or heteroaryl, in each case mono- or polysubstituted or unsubstituted;

$OR^{11}$, $OC(O)R^{11}$, $C(O)R^{11}$, $C(O)OR^{11}$, $C(O)NR^{11}R^{11'}$, $NR^{11}R^{11'}$, $S(O_2)R^{11}$ or $SR^{11}$, wherein $R^{11}$ and $R^{11'}$ independently represent H; $C_1$–$C_{18}$ alkyl, $C_2$–$C_{18}$ alkenyl or $C_2$–$C_{18}$ alkynyl, in each case branched or unbranched, mono- or polysubstituted or unsubstituted; $C_3$–$C_8$ cycloalkyl, saturated or unsaturated, mono- or polysubstituted or unsubstituted, or a corresponding heterocycle, in which at least one C atom in the ring is replaced by N, S or O; alkylaryl or alkylheteroaryl, in each case mono- or polysubstituted or unsubstituted; aryl or heteroaryl, in each case mono- or polysubstituted or unsubstituted;

$R^5$ represents

H; $C_1$–$C_{18}$ alkyl, $C_2$–$C_{18}$ alkenyl or $C_2$–$C_{18}$ alkynyl, in each case branched or unbranched, mono- or polysubstituted or unsubstituted; $C_3$–$C_8$ cycloalkyl, saturated or unsaturated, mono- or polysubstituted or unsubstituted, or a corresponding heterocycle, in which at least one C atom in the ring is replaced by N, S or O; alkylaryl or alkylheteroaryl, in each case mono- or polysubstituted or unsubstituted; aryl or heteroaryl, in each case mono- or polysubstituted or unsubstituted;

$R^6$ represents $R^{12}$ or $ZR^{12}$ with $Z=C_1-C_6$ alkyl, $C_2-C_6$ alkenyl or $C_2-C_6$ alkynyl, in each case branched or unbranched, mono- or polysubstituted or unsubstituted, with $R^{12}$ selected from among H; $C_1-C_{12}$ alkyl, $C_2-C_{12}$ alkenyl or $C_2-C_{12}$ alkynyl, in each case branched or unbranched, mono- or polysubstituted or unsubstituted; $C_3-C_8$ cycloalkyl, saturated or unsaturated, mono- or polysubstituted or unsubstituted, or a corresponding heterocycle, in which at least one C atom in the ring is replaced by S, O or N; aryl or heteroaryl, in each case mono- or polysubstituted or unsubstituted;

$C(O)R^{13}$, $C(O)OR^{13}$, $C(S)R^{13}$, $C(S)OR^{13}$ or $S(O^2)R^{13}$ wherein $R^{13}$ represents H; $C_1-C_{10}$ alkyl, $C_2-C_{10}$ alkenyl or $C_2-C_{10}$ alkynyl, in each case branched or unbranched, mono- or polysubstituted or unsubstituted; $C_3-C_8$ cycloalkyl, saturated or unsaturated, mono- or polysubstituted or unsubstituted, or a corresponding heterocycle, in which at least one C atom in the ring is replaced by S, O or N; alkylaryl or alkylheteroaryl, in each case mono- or polysubstituted or unsubstituted; aryl or heteroaryl, in each case mono- or polysubstituted or unsubstituted, in particular phenethyl, 1-adamantyl, 2-adamantyl, 1-naphthyl or 2-naphthyl, 2-, 3- or 4-pyridyl; thiazolyl;

$SR^{14}$ wherein $R^{14}$ represents aryl or heteroaryl, in each case mono- or polysubstituted or unsubstituted, $C(O)NR^{15}R^{16}$, $C(O)NR^{15}NR^{16}R^{17}$, $C(NR^{15})NR^{16}R^{17}$, $C(S)NR^{15}R^{16}$ or $C(S)NR^{15}NR^{16}R^{17}$, wherein $R^{15}$, $R^{16}$ and $R^{17}$ independently represent H; $C_1-C_{18}$ alkyl, $C_2-C_{18}$ alkenyl or $C_2-C_{18}$ alkynyl, in each case branched or unbranched, mono- or polysubstituted or unsubstituted; $C_3-C_8$ cycloalkyl, saturated or unsaturated, mono- or polysubstituted or unsubstituted, or a corresponding heterocycle, in which at least one C atom in the ring is replaced by S, O or N; alkylaryl or alkylheteroaryl, in each case mono- or polysubstituted or unsubstituted; aryl or heteroaryl, in each case mono- or polysubstituted or unsubstituted;

$R^7$, $R^8$, $R^9$ and $R^{10}$ independently represent

H, F, Cl, Br, I, CN, $NO_2$; $C_1-C_{10}$ alkyl, $C_2-C_{10}$ alkenyl or $C_2-C_{10}$ alkynyl, in each case branched or unbranched, mono- or polysubstituted or unsubstituted;

$OR^{18}$, $OC(O)R^{18}$, $OC(S)R^{18}$, $C(O)R^{18}$, $C(O)OR^{18}$, $C(S)R^{18}$, $C(S)OR^{18}$, $SR^{18}$, $S(O)R^{18}$ or $S(O_2)R^{18}$, wherein $R^{18}$ represents H; $C_1-C_{10}$ alkyl, $C_2-C_{10}$ alkenyl or $C_2-C_{10}$ alkynyl, in each case branched or unbranched, mono- or polysubstituted or unsubstituted; $C_3-C_8$ cycloalkyl, saturated or unsaturated, mono- or polysubstituted or unsubstituted, or a corresponding heterocycle, in which at least one C atom in the ring is replaced by S, O or N; alkylaryl or alkylheteroaryl, in each case mono- or polysubstituted or unsubstituted; aryl or heteroaryl, in each case mono- or polysubstituted or unsubstituted;

$NR^{19}R^{20}$, $NR^{19}C(O)R^{20}$, $C(NR^{19})NR^{20}R^{21}$, $NR^{19}C(S)R^{20}$, $C(S)NR^{19}R^{20}$ or $C(S)NR^{19}NR^{20}R^{21}$ or $S(O_2)NR^{19}R^{20}$, wherein $R^{19}$, $R^{20}$ and $R^{21}$ independently represent H, O; $C_1-C_{18}$ alkyl, $C_2-C_{18}$ alkenyl or $C_2-C_{18}$ alkynyl, in each case branched or unbranched, mono- or polysubstituted or unsubstituted; $C_3-C_8$ cycloalkyl, saturated or unsaturated, mono- or polysubstituted or unsubstituted, or a corresponding heterocycle, in which at least one C atom in the ring is replaced by S, O or N, alkylaryl or alkylheteroaryl, in each case mono- or polysubstituted or unsubstituted; aryl or heteroaryl, in each case mono- or polysubstituted or unsubstituted; or $R^{19}$ and $R^{20}$ or $R^{20}$ and $R^{21}$ together form a $C_3-C_8$ cycloalkyl, saturated or unsaturated, mono- or polysubstituted or unsubstituted, or a corresponding heterocycle, in which at least one C atom in the ring is replaced by S, O or N; or $R^7$ and $R^8$, $R^8$ and $R^9$ or $R^9$ and $R^{10}$ together form $=CR^{22}-CH=CH-CH=$ or $=CH-CR^{22}=CH-CH=$, wherein $R^{22}$ represents H, F, Cl, Br, I, OH or $C_1-C_{10}$ alkyl, $C_2-C_{10}$ alkenyl or $C_2-C_{10}$ alkynyl, in each case branched or unbranched, mono- or polysubstituted or unsubstituted, or a salt thereof with a physiologically acceptable acid.

2. The compound of claim 1, wherein said compound is present in the form of a free base.

3. The compound of claim 1, wherein said compound is present in the form of a salt with a base.

4. The compound of claim 1, wherein said compound is present in the form of a mixture of stereoisomers.

5. The compound of claim 1, wherein said compound is present in the form of a racemic mixture.

6. The compound of claim 1, wherein said compound is present in the form of a solvate.

7. The compound of claim 1, wherein said compound is present in the form of a hydrate.

8. A 5,6,6a,11b-tetrahydro-7-oxa-5-aza-benzo[c]fluorene-6-carboxylic acid compound according to claim 1, wherein $R^6$ represents H; $C_1-C_{10}$ alkyl, either unsubstituted or mono- or polysubstituted; or phenyl, either unsubstituted or mono- or polysubstituted.

9. A 5,6,6a,11b-tetrahydro-7-oxa-5-aza-benzo[c]fluorene-6-carboxylic acid compound according to claim 8, wherein $R^6$ represents H, $CH_3$ or $C_2H_5$.

10. A 5,6,6a,11b-tetrahydro-7-oxa-5-aza-benzo[c]fluorene-6-carboxylic acid compound according to claim 1, wherein $R^5$ represents H; $C_1-C_4$ alkyl, branched or unbranched, mono- or polysubstituted or unsubstituted; or phenyl, benzyl, or phenethyl, mono- or polysubstituted or unsubstituted.

11. A 5,6,6a,11b-tetrahydro-7-oxa-5-aza-benzo[c]fluorene-6-carboxylic acid compound according to claim 10, wherein $R^5$ represents H, $CH_3$ or $C_2H_5$.

12. A 5,6,6a,11b-tetrahydro-7-oxa-5-aza-benzo[c]fluorene-6-carboxylic acid compound according to one of claim 1, wherein $R^7$, $R^8$, $R^9$ and $R^{10}$ independently represent H, F, Cl, Br, I, CN, $NO_2$; $C_1-C_6$ alkyl, $C_2-C_6$ alkenyl or $C_2-C_6$ alkynyl, in each case branched or unbranched, mono- or polysubstituted or unsubstituted; or OR$^{18}$, C(O)R$^{18}$, C(O)OR$^{18}$ or SR$^{18}$, wherein R$^{18}$ represents H; C$_1$–C$_4$ alkyl, branched or unbranched, mono- or polysubstituted or unsubstituted; aryl, mono- or polysubstituted or unsubstituted.

13. A 5,6,6a,11b-tetrahydro-7-oxa-5-aza-benzo[c]fluorene-6-carboxylic acid compound according to claim 12, wherein R$^7$, R$^8$, R$^9$ and R$^{10}$ independently represent H, F, Cl, Br, I, CN; C$_1$–C$_4$ alkyl, branched or unbranched, mono- or polysubstituted or unsubstituted; or OR$^{18}$ or SR$^{18}$, wherein R$^{18}$ represents H; C$_1$–C$_4$ alkyl, branched or unbranched, mono- or polysubstituted or unsubstituted; phenyl, mono- or polysubstituted or unsubstituted.

14. A 5,6,6a,11b-tetrahydro-7-oxa-5-aza-benzo[c]fluorene-6-carboxylic acid compound according to claim 13, wherein R7, R8, R9 and R10 independently represent H, F, Cl, Br, I, CN; CH$_3$, CF$_3$, t-butyl, i-butyl, OH, —OCH$_3$, —OCF$_3$, —SCH$_3$, or —O-phenyl.

15. A 5,6,6a,11b-tetrahydro-7-oxa-5-aza-benzo[c]fluorene-6-carboxylic acid compound according to claim 1, wherein R$^7$, R$^8$ and R$^{10}$ represent H and R$^9$ represents Cl or R$^7$ and R$^9$ represent H and R$^8$ and R$^{10}$ represent Cl.

16. A 5,6,6a,11b-tetrahydro-7-oxa-5-aza-benzo[c]fluorene-6-carboxylic acid compound according to claim 1, wherein

R$^5$=H,

R$^6$=H,

R$^7$=H,

R$^8$=Cl,

R$^9$=H and

R$^{10}$=Cl.

17. A 5,6,6a,11b-tetrahydro-7-oxa-5-aza-benzo[c]fluorene-6-carboxylic acid compound according to claim 1, wherein at least one of R$^1$, R$^2$, R$^3$ and R$^4$ independently represent H, F, Cl, Br, I, CN, NO$_2$; C$_1$–C$_6$ alkyl, C$_2$–C$_6$ alkenyl or C$_2$–C$_6$ alkynyl, in each case branched or unbranched, mono- or polysubstituted or unsubstituted; or OR$^{11}$, OC(O)R$^{11}$, C(O)R$^{11}$, C(O)OR$^{11}$, C(O)NR$^{11}$R$^{11'}$, NR$^{11}$R$^{11'}$, S(O$_2$)R$^{11}$ or SR$^{11}$, wherein R$^{11}$ and R$^{11'}$ independently represent H; C$_1$–C$_6$ alkyl, C$_2$–C$_6$ alkenyl or C$_2$–C$_6$ alkynyl, in each case branched or unbranched, mono- or polysubstituted or unsubstituted.

18. A 5,6,6a,11b-tetrahydro-7-oxa-5-aza-benzo[c]fluorene-6-carboxylic acid compound according to claim 17, wherein at least one of R$^1$, R$^2$, R$^3$ and R$^4$ independently represent H, F, Cl, Br, I, CN, NH$_2$, NO$_2$; C$_1$–C$_4$ alkyl, C$_2$–C$_4$ alkenyl or C$_2$–C$_4$ alkynyl, in each case branched or unbranched, mono- or polysubstituted or unsubstituted; or OR$^{11}$, C(O)OR$^{11}$ or SR$^{11}$, wherein R$^{11}$ represents H; C$_1$–C$_4$ alkyl, C$_2$–C$_4$ alkenyl or C$_2$–C$_4$ alkynyl, in each case branched or unbranched, mono- or polysubstituted or unsubstituted.

19. A 5,6,6a,11b-tetrahydro-7-oxa-5-aza-benzo[c]fluorene-6-carboxylic acid compound according to claim 17, wherein at least one of R$^1$, R$^2$, R$^3$ and R$^4$ independently represent H, F, Cl, Br, I, CN, NH$_2$; C$_1$–C$_4$ alkyl, branched or unbranched, mono- or polysubstituted or unsubstituted; or SH; OR$^{11}$ or C(O)OR$^{11}$, wherein R$^{11}$ represents H; C$_1$–C$_4$ alkyl, branched or unbranched, mono- or polysubstituted or unsubstituted.

20. A 5,6,6a,11b-tetrahydro-7-oxa-5-aza-benzo[c]fluorene-6-carboxylic acid compound according to claim 17, wherein at least one of R$^1$, R$^2$, R$^3$ and R$^4$ independently represent H, F, Cl, Br, I, CN, NH$_2$, CH$_3$, C$_2$H$_5$, n-propyl, i-propyl, i-butyl, sec.-butyl, n-butyl, t-butyl, CF$_3$, CHF$_2$, SH, OH, OCH$_3$, OC$_2$H$_5$, C(O)OH, C(O)OCH$_3$ or C(O)OC$_2$H$_5$.

21. A 5,6,6a,11b-tetrahydro-7-oxa-5-aza-benzo[c]fluorene-6-carboxylic acid compound according to claim 1, wherein said compound is selected from the group consisting of:

1,3-Dichloro-5,6,6a,11b-tetrahydro-7-oxa-5-aza-benzo[c]fluorene-6-carboxylic acid;

1,3-Dichloro-10-methoxy-5,6,6a,11b-tetrahydro-7-oxa-5-aza-benzo[c]fluorene-6-carboxylic acid;

1,3-Dichloro-8-methyl-5,6,6a,11b-tetrahydro-7-oxa-5-aza-benzo[c]fluorene-6-carboxylic acid;

1,3-Dichloro-8-ethyl-5,6,6a,11b-tetrahydro-7-oxa-5-aza-benzo[c]fluorene-6-carboxylic acid;

1,3-Dichloro-8-ethyl-5,6,6a,11b-tetrahydro-7-oxa-5-aza-benzo[c]fluorene-6-carboxylic acid;

1,3-Dichloro-8-fluoro-5,6,6a,11b-tetrahydro-7-oxa-5-aza-benzo[c]fluorene-6-carboxylic acid;

1,3,8-Trichloro-5,6,6a,11b-tetrahydro-7-oxa-5-aza-benzo[c]fluorene-6-carboxylic acid;

8-Bromo-1,3-dichloro-5,6,6a,11b-tetrahydro-7-oxa-5-aza-benzo[c]fluorene-6-carboxylic acid;

8-Iodo-1,3-dichloro-5,6,6a,11b-tetrahydro-7-oxa-5-aza-benzo[c]fluorene-6-carboxylic acid;

1,3-Dichloro-5,6,6a,11b-tetrahydro-7-oxa-5-aza-benzo[c]fluorene-6,8-dicarboxylic acid;

1,3-Dichloro-10-methyl-5,6,6a,11b-tetrahydro-7-oxa-5-aza-benzo[c]fluorene-6-carboxylic acid;

1,3-Dichloro-10-fluoro-5,6,6a,11b-tetrahydro-7-oxa-5-aza-benzo[c]fluorene-6-carboxylic acid;

1,3,10-Trichloro-5,6,6a,11b-tetrahydro-7-oxa-5-aza-benzo[c]fluorene-6-carboxylic acid;

10-Bromo-1,3-dichloro-5,6,6a,11b-tetrahydro-7-oxa-5-aza-benzo[c]fluorene-6-carboxylic acid;

10-Iodo-1,3-dichloro-5,6,6a,11b-tetrahydro-7-oxa-5-aza-benzo[c]fluorene-6-carboxylic acid;

1,3-Dichloro-5,6,6a,11b-tetrahydro-7-oxa-5-aza-benzo[c]fluorene-6,10-dicarboxylic acid or 1,3-Dichloro-10-cyano-5,6,6a,11b-tetrahydro-7-oxa-5-aza-benzo[c]fluorene-6-carboxylic acid, or a salt thereof with a physiologically acceptable acid.

22. A 5,6,6a,11b-tetrahydro-7-oxa-5-aza-benzo[c]fluorene-6-carboxylic acid compound according to claim 21, wherein said compound is 1,3-Dichloro-5,6,6a,11b-tetrahydro-7-oxa-5-aza-benzo[c]fluorene-6-carboxylic acid or a salt thereof with a physiologically acceptable acid.

23. A 5,6,6a,11b-tetrahydro-7-oxa-5-aza-benzo[c]fluorene-6-carboxylic acid compound according to claim 1, wherein said compound is present as an alkali metal salt or an inorganic acid salt.

24. A 5,6,6a,11b-tetrahydro-7-oxa-5-aza-benzo[c]fluorene-6-carboxylic acid compound according to claim 23, wherein said alkali metal salt is a potassium or sodium salt, and wherein said inorganic acid salt is a hydrochloride salt.

25. A process for preparing a 5,6,6a,11b-tetrahydro-7-oxa-5-aza-benzo[c]fluorene-6-carboxylic acid compound corresponding to formula I of claim 1 wherein $R^6$=H,

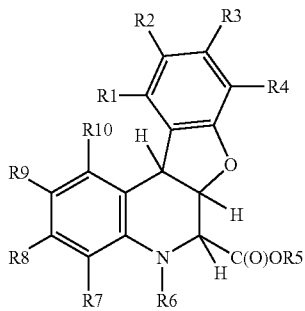

comprising the step of:
reacting an aniline corresponding to formula II, a glyoxalic acid ester or glyoxalic acid compound corresponding to formula III and a benzofuran corresponding to formula IV, with trifluoroacetic acid.

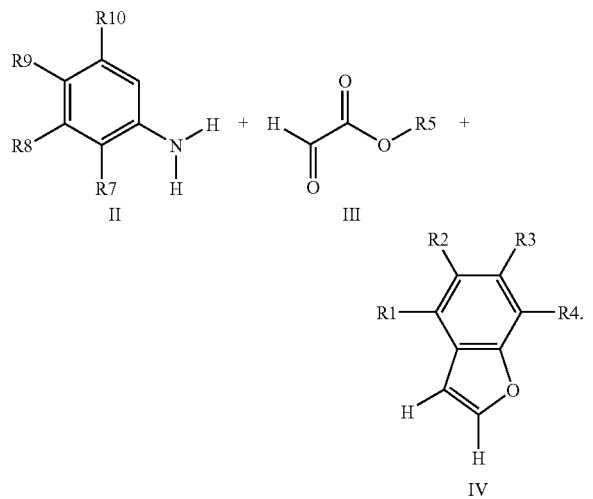

26. The process of claim 25, wherein said step of reacting is carried out at a temperature between 0° C. and 100° C.

27. The process of claim 25, wherein at least one of $R^1$, $R^2$, $R^3$, $R^4$, $R^5$, $R^7$, $R^8$, $R^9$ or $R^{10}$ are independently provided with a protective group.

28. The process of claim 25, wherein the duration of the reaction is 0.25–12 hours.

29. The process of claim 25, wherein the duration of the reaction is no longer than 2 hours.

30. The process of claim 25, wherein the reaction is carried out at a temperature of between 20 and 40° C.

31. The process of claim 30, wherein the reaction is carried out at room temperature.

32. The process of claim 25, wherein the reaction is a single-vessel reaction.

33. A process for preparing a 5,6,6a,11b-tetrahydro-7-oxa-5-aza-benzo[c]fluorene-6-carboxylic acid compound according to formula 1 of claim 1, wherein $R^6 \neq H$,

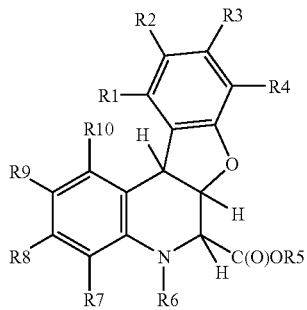

comprising the steps of:
reacting an aniline of formula II, a glyoxalic acid ester or glyoxalic acid compound corresponding to formula III and a benzofuran corresponding to formula IV, with trifluoroacetic acid to form a reaction product wherein $R^6$=H, and

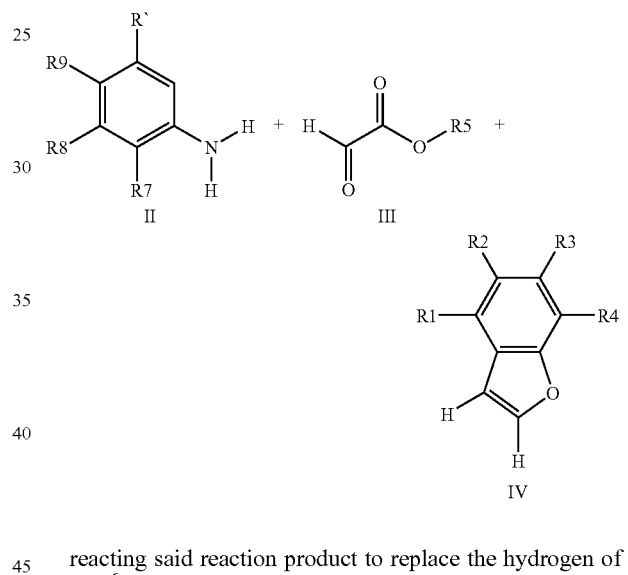

reacting said reaction product to replace the hydrogen of $R^6$ with a group selected from
$R^{12}$ or $ZR^{12}$ with Z=$C_1$–$C_6$ alkyl, $C_2$–$C_6$ alkenyl or $C_2$–$C_6$ alkynyl, in each case branched or unbranched, mono- or polysubstituted or unsubstituted, with $R^{12}$ selected from among
H; $C_1$–$C_{12}$ alkyl, $C_2$–$C_{12}$ alkenyl or $C_2$–$C_{12}$ alkynyl, in each case branched or unbranched, mono- or polysubstituted or unsubstituted; $C_3$–$C_8$ cycloalkyl, saturated or unsaturated, mono- or polysubstituted or unsubstituted, or a corresponding heterocycle, in which at least one C atom in the ring is replaced by S, O or N; aryl or heteroaryl, in each case mono- or polysubstituted or unsubstituted;
$C(O)R^{13}$, $C(O)OR^{13}$, $C(S)R^{13}$, $C(S)OR^{13}$ or $S(O_2)R^{13}$ wherein $R^{13}$ represents
H; $C_1$–$C_{10}$ alkyl, $C_2$–$C_{10}$ alkenyl or $C_2$–$C_{10}$ alkynyl, in each case branched or unbranched, mono- or polysubstituted or unsubstituted; $C_3$–$C_8$ cycloalkyl, saturated or unsaturated, mono- or polysubstituted or unsubstituted, or a corresponding heterocycle, in which at least one C atom in the ring is replaced by S, O or N; alkylaryl or alkylheteroaryl, in each case mono- or polysubstituted or unsubstituted; aryl or heteroaryl, in each case mono- or polysubstituted or unsubstituted, in particular phenethyl, 1-adamantyl, 2-adamantyl, 1-naphthyl or 2-naphthyl, 2-, 3- or 4-pyridyl; thiazolyl;

$SR^{14}$ wherein $R^{14}$ represents aryl or heteroaryl, in each case mono- or polysubstituted or unsubstituted, $C(O)NR^{15}R^{16}$, $C(O)NR^{15}NR^{16}R^{17}$, $C(NR^{15})NR^{16}R^{17}$, $C(S)NR^{15}R^{16}$ or $C(S)NR^{15}NR^{16}R^{17}$, wherein $R^{15}$, $R^{16}$ and $R^{17}$ independently represent H; $C_1$–$C_{18}$ alkyl, $C_2$–$C_{18}$ alkenyl or $C_2$–$C_{18}$ alkynyl, in each case branched or unbranched, mono- or polysubstituted or unsubstituted; $C_3$–$C_8$ cycloalkyl, saturated or unsaturated, mono- or polysubstituted or unsubstituted, or a corresponding heterocycle, in which at least one C atom in the ring is replaced by S, O or N; alkylaryl or alkylheteroaryl, in each case mono- or polysubstituted or unsubstituted; aryl or heteroaryl, in each case mono- or polysubstituted or unsubstituted.

34. A process according to claim 25, wherein in at least one of the aniline corresponding to formula II, the glyoxalic acid ester or glyoxalic acid compound corresponding to formula III or the benzofuran corresponding to formula IV, $R^1$, $R^2$, $R^3$, $R^4$, $R^5$, $R^7$, $R^8$, $R^9$ or $R^{10}$ are independently provided with a protective group, said protective group being selected from the group consisting of OSi(Ph)$_2$tert.-butyl to replace an OH group;
p-methoxybenzyl to replace an SH-group and
NO$_2$ to replace an NH$_2$ group and
before a purification step,
at least one OSi(Ph)$_2$tert.-butyl group is cleaved with tetrabutylammonium fluoride in tetrahydrofuran;
at least one S-p-methoxybenzyl group is cleaved with a metal amide or
at least one NO$_2$ group is reduced to NH$_2$.

35. A process according to claim 34, wherein said metal amide is sodium amide.

36. A process according to claim 34, wherein, before purification, all OSi(Ph)$_2$tert.-butyl groups are cleaved with tetrabutylammonium fluoride in tetrahydrofuran;
all S-p-methoxybenzyl groups are cleaved with a metal amide or
all NO$_2$ groups are reduced to NH$_2$.

37. A process according to claims 25, wherein a product of the process with at least one C(O)OCH$_3$ or C(S)OCH$_3$ group or a product of the process wherein $R^5$=$C_{1-4}$ alkyl, is saponified with KOH solution or NaOH solution in methanol or ethanol at a temperature of from 0° C. to 100° C.

38. A process according to claim 37, wherein said temperature is from 40° C. to 60° C.

39. A process according to claim 37, wherein in said product of the process $R^5$=CH$_3$ or C$_2$H$_5$.

40. A pharmaceutical composition, comprising:
at least one 5,6,6a,11b-tetrahydro-7-oxa-5-aza-benzo[c]fluorene-6-carboxylic acid compound corresponding to formula I of claim 1 or a salt thereof with a physiologically tolerated acid and an auxiliary agent.

41. The pharmaceutical composition of claim 40, wherein said compound is present in the form of a free base.

42. The pharmaceutical composition of claim 40, wherein said compound is present in the form of a pure diastereoisomer.

43. The pharmaceutical composition of claim 40, wherein said compound is present in the form of a mixture of stereoisomers.

44. The pharmaceutical composition of claim 40, wherein said compound is present in the form of a racemic mixture.

45. The pharmaceutical composition of claim 40, wherein said compound is present in the form of a solvate.

46. The pharmaceutical composition of claim 40, wherein said compound is present in the form of a hydrate.

47. A method of treating pain in a mammal, said method comprising administering to said mammal an effective pain alleviating amount of a compound according to claim 1.

48. The method of claim 47, wherein said pain is neuropathic or chronic pain.

49. The method of claim 47, wherein said pain is pain from a migraine.

* * * * *